(12) United States Patent
    Bugelski et al.

(10) Patent No.: US 8,277,809 B2
(45) Date of Patent: Oct. 2, 2012

(54) CXCL13 ANTAGONISTS AND THEIR USE FOR THE TREATMENT OF INFLAMMATORY DISEASES

(75) Inventors: Peter Bugelski, Pottstown, PA (US); Anuk Das, Berwyn, PA (US); Donald E. Griswold, North Wales, PA (US); Bailin Liang, Gilbertsville, PA (US); Li Li, Downingtown, PA (US); Robert T. Sarisky, Lansdale, PA (US); Xiaozhou Shang, West Chester, PA (US)

(73) Assignee: Centocor, Inc., Malvern, PA (US)

( * ) Notice: Subject to any disclaimer, the term of this patent is extended or adjusted under 35 U.S.C. 154(b) by 563 days.

(21) Appl. No.: 11/738,019

(22) Filed: Apr. 20, 2007

(65) Prior Publication Data

US 2008/0014201 A1    Jan. 17, 2008

Related U.S. Application Data

(60) Provisional application No. 60/794,018, filed on Apr. 21, 2006, provisional application No. 60/909,128, filed on Mar. 30, 2007.

(51) Int. Cl.
    *A61K 39/395* (2006.01)
(52) U.S. Cl. .............. 424/145.1; 424/141.1; 424/130.1
(58) Field of Classification Search .................. None
    See application file for complete search history.

(56) References Cited

U.S. PATENT DOCUMENTS

| | | | | |
|---|---|---|---|---|
| 5,919,452 | A * | 7/1999 | Le et al. ............... | 424/133.1 |
| 7,235,239 | B2 | 6/2007 | Guegler et al. | |
| 7,390,884 | B2 * | 6/2008 | Segal et al. ........... | 530/387.1 |
| 2004/0170628 | A1 | 9/2004 | Lillard et al. | |
| 2005/0249723 | A1 | 11/2005 | Lazar et al. | |
| 2009/0136512 | A1 | 5/2009 | Bugelski et al. | |

FOREIGN PATENT DOCUMENTS

| | | |
|---|---|---|
| WO | WO99/28464 A1 | 6/1999 |
| WO | WO03/035105 A2 | 5/2003 |
| WO | WO03/047420 A2 | 6/2003 |
| WO | WO2007/122402 A1 | 11/2007 |

OTHER PUBLICATIONS

Strom et al. In Therapeutic Immunology, Austen et al. (Ed.) Blackwell Science, Cambridge MA, 1996; see pp. 451-456.*
Muller, et al., "The impact of CCR7 and CXCR5 on lymphoid organ development and systemic immunity," Immunol Rev, 2003, 195: 117-135.
Buckley, et al., "Michael Mason prize essay 2003. Why do leucocytes accumulate within chronically inflamed joints?" Rheumatology (Oxford), 2003, 42(12): 1433-1444.
Salomonsson, et al., "Cellular basis of ectopic germinal center formation and autoantibody production in the target organ of patients with Sjogren's syndrome," Arthritis Rheum, 2003, 48(11): 3187-3201.
Sato, et al., "Aberrant B1 cell migration into the thymus results in activation of CD4 T cells through its potent antigen-presenting activity in the development of murine lupus," Eur J Immunol, 2004, 34(12): 3346-3358.
Ito, et al., "Defective B1 cell homing to the peritoneal cavity and preferential recruitment of B1 cells in the target organs in a murine model for systemic lupus erythematosus," J Immunol, 2004, 172(6): 3628-3634.
Carlsen, et al., "Monocyte-like and mature macrophages produce CXCL13 (B cell-attracting chemokine 1) in inflammatory lesions with lymphoid neogenesis," Blood, 2004, 104(10): 3021-3027.
Carlsen, et al., "B cell attracting chemokine 1 (CXCL13) and its receptor CXCR5 are expressed in normal and aberrant gut associated lymphoid tissue," Gut, 2002, 51(3): 364-371.
Corcione, et al., "Recapitulation of B cell differentiation in the central nervous system of patients with multiple sclerosis," Proc Natl Acad Sci U S A, 2004, 101(30): 11064-11069.
Serafini, et al., "Detection of ectopic B-cell follicles with germinal centers in the meninges of patients with secondary progressive multiple sclerosis," Brain Pathol, 2004, 14(2): 164-174.
Magliozzi, et al., "Intracerebral expression of CXCL13 and BAFF is accompanied by formation of lymphoid follicle-like structures in the meninges of mice with relapsing experimental autoimmune encephalomyelitis," J Neuroimmunol, 2004, 148(1-2): 11-23.
Luther, et al., "Differing activities of homeostatic chemokines CCL19, CCL21, and CXCL12 in lymphocyte and dendritic cell recruitment and lymphoid neogenesis," J Immunol, 2002, 169(1): 424-433.
Hjelmstrom, et al., "Lymphoid tissue homing chemokines are expressed in chronic inflammation," Am J Pathol, 2000, 156(4): 1133-1138.
Bistrup, et al., "Detection of a sulfotransferase (HEC-GlcNAc6ST) in high endothelial venules of lymph nodes and in high endothelial venule-like vessels within ectopic lymphoid aggregates: relationship to the MECA-79 epitope," Am J Pathol, 2004, 164(5): 1635-1644.
Aust, et al., "The role of CXCR5 and its ligand CXCL13 in the compartmentalization of lymphocytes in thyroids affected by autoimmune thyroid diseases," Eur J Endocrinol, 2004, 150(2): 225-234.
Armengol, et al., "Chemokines determine local lymphoneogenesis and a reduction of circulating CXCR4+ T and CCR7 B and T lymphocytes in thyroid autoimmune diseases," J Immunol, 2003, 170(12): 6320-6328.
Hogg, et al., "The nature of small-airway obstruction in chronic obstructive pulmonary disease," N Engl J Med, 2004, 350(26): 2645-2653.
Turato, et al., "Pathogenesis and pathology of COPD," Respiration, 2001, 68(2): 117-128.
Lundblad, et al., "TNF-{alpha} Over-expression in Lung Disease: a Single Cause Behind a Complex Phenotype," Am J Respir Crit Care Med, 2005, 171: 1363-1370.

(Continued)

*Primary Examiner* — Sharon Wen
(74) *Attorney, Agent, or Firm* — Eric Dichter

(57) ABSTRACT

Methods of treating disorders related to CXCL13 activity utilize CXCL13 antagonists and, optionally, TNFα antagonists, such as antibodies, including specified portions or variants, polypeptides, polynucleotides, siRNA, shRNA, ribozymes, and DNAzymes. Disorders related to CXCL13 activity include inflammatory disorders, such as pulmonary disorders, for example, asthma, emphysema, and COPD, and systemic lupus erythematosus.

15 Claims, 8 Drawing Sheets

OTHER PUBLICATIONS

Yang, et al., "*Local macrophage proliferation in human glomerulonephritis*," Kidney Int. (1998), 54(1): 143-151.

Rovin, et al., "*Plasma, urine and renal expression of adiponectin in human systemic lupus erythematosus*," Kidney Int., 2005, 68(4): 1825-1833.

GenBank Accession No. NM_006419 (Jan. 14, 2007).

Lukacs, et al., "*Leukocyte Infiltration in Allergic Airway Inflammation*," American Journal of Respiratory and Cell Molecular Biology, 1995, 13: 1-6.

Busse, et al., "*Mechanisms of Persistent Airway Inflammation in Asthma: A Role for T Cells and T-Cell Products*," American Journal of Respiratory and Critical Care Medicine, 1995, 152: 388-393.

Peter J. Barnes, "*Cytokines as mediators of Chronic Asthma*," American Journal of Respiratory and Critical Care Medicine, 1994, 150: S42-S49.

Lukacs, et al., "*Activation and regulation of chemokines in allergic airway inflammation*," Journal of Leukocyte Biology, 1996, 59: 13-17.

Minor, et al., "*Viruses as Precipitants of Asthmatic Attacks in Children*," Journal of American Medical Association, 1974, 227(3): 292-298.

Ferreri, et al., "*Release of Leukotrienes, Prostaglandins, and Histamine into Nasal Secretions of Aspirin-sensitive Asthmatics during Reaction to Aspirin*," American Review of Respiratory Disease, 1988, 137: 847-854.

Finnerty, et al., "*Role of Leukotrienes in Exercise-Induced Asthma: Inhibitory Effect of ICI 204219, a Potent Leukotriene D, Receptor antagonist*," American Review of Respiratory Disease, 1992, 145: 746-749.

Venables, et al., "*Occupational asthma*," Lancet, 1997, 349: 1465-1469.

Barnes, et al., "*Inflammatory Mediators of Asthma: An Update*," Pharmacological Reviews, 1998, 50(4): 515-596.

Chung, et al., "*Cytokines in asthma*," Thorax, 1999, 54: 825-857.

Zimmermann, et al., "*Dissection of experimental asthma with DNA microarray analysis identifies arginase in asthma pathogenesis*," The Journal of Clinical Investigation, 2003, 111(12): 1863-1874.

Mary Jane Cunningham, "*Genomics and proteomics: The new millennium of drug discovery and development*," Journal of Pharmacological and Toxicological Methods, 2000, 44: 291-300.

Filippi, et al., "*Identification, localization and functional activity of oxytocin receptors in epididymis*," Molecular and Cellular Endocrinology, 2002, 193: 89-100.

Zou, et al., "*Microarray profile of differentially expressed genes in a monkey model of allergic asthma*," Genome Biology, 2002, 3(5): 0020.1-0020.13.

Daikh, et al., "*Cutting Edge: Reversal of Murine Lupus Nephritis with CTLA4Ig and Cyclophosphamide*," Journal of Immunology, 2001, 166: 2913-2916.

Piao, et al., "*TNF Receptor-Associated Factor 2-Dependent Canonical Pathway Is Crucial for the Development of Peyer's Patches*," Journal of Immunology, (2007), 178: 2272-2277.

Ngo, et al., "*Lymphotoxin α/β and Tumor Necrosis Factor Are Required for Stromal Cell Expression of Homing Chemokines in B and T Cell Areas of the Spleen*," Journal of Experimental Medicine (1999), 189(2): 403-412.

Schiffer, et al., "*Short Term Administration of Costimulatory Blockade and Cyclophosphamide Induces Remission of Systemic Lupus Erythematosus Nephritis in NZB/W F1 Mice by a Mechanism Downstream of Renal Immune Complex Deposition*," Journal of Immunology (2003), 171: 489-497.

Browning, et al., "*Inhibition of the lymphotoxin pathway as a therapy for autoimmune disease*," Immunological Review (2008), 223: 202-220.

PCT International Search Report dated Oct. 2, 2008.

Krumbholz, et al., "Chemokines in multiple sclerosis: CXCL12 and CXCL13 up-regulation is differentially linked to CNS immune cell recruitment," Brain, 129:200-210 (2006).

\* cited by examiner

CXCL13 ANTAGONISTS AND THEIR USE FOR THE TREATMENT OF INFLAMMATORY DISEASES

CROSS-REFERENCE TO RELATED APPLICATIONS

This application claims the benefit of U.S. Provisional Application Nos. 60/794,018, filed 21 Apr. 2006 and 60/909,128, filed 30 Mar. 2007, the entire contents of which are incorporated herein by reference.

FIELD OF THE INVENTION

The present invention relates to CXCL13 antagonists and a method of using CXCL13 antagonists to treat pulmonary disorders and symptoms, and conditions, as well as related diseases and conditions. The invention more specifically relates to methods of treating such diseases by the use of CXCL13 antagonists alone or along with TNFα antagonists, such as interfering RNA, DNAzymes, and antibodies directed toward CXCL13, including specified portions or variants, specific for at least one protein or fragment thereof, in an amount effective to inhibit CXCL13 activity. The present invention also relates to a method of using CXCL13 antagonists and TNFα antagonists to treat an animal with other inflammatory diseases, such as systemic lupus erythematosus.

BACKGROUND OF THE INVENTION

Asthma is a complex, chronic disorder, with a genetic and an environmental component (1). It is characterized by reversible airway obstruction, airway hyperresponsiveness, airway inflammation and remodeling (2). Asthma affects an estimated 15 million Americans and the morbidity and mortality associated with it is on the rise in industrialized countries (3,4). Inflammation in the airway of an allergic asthmatic is associated with the mucosal infiltration of T helper (Th)2 subset of $CD4^+$ T cells and eosinophils (5,6). The interaction between these cells leads to the production of various pro-inflammatory mediators involved in the pathogenesis of asthma (7,8). Other forms of asthma are those that are induced by exercise, viruses, aspirin and occupation. Although the mechanism responsible for these forms of asthma might involve Th2 lymphocytes and cytokines it might be triggered differently (9-12). Many cytokines and chemokines are involved in the pathogenesis of asthma (13,14). Specifically, the Th2 derived cytokines (interleukin 4, 5, 9 and 13) play an important role in allergic diseases including asthma.

Chronic obstructive pulmonary disease (COPD) is a chronic pulmonary inflammation characterized by the infiltration of neutrophils, macrophages, B and T cells. These immunocompetent cells are activated by a variety of cytokines and chemokines that are released in the lung in response to a prolonged exposure to toxic gases and particles (15). Bronchitis and emphysema, together with irreversible airflow obstruction, are the clinical manifestations of the disease. No known agents delay the accelerated decline in pulmonary function that characterizes COPD.

Recently, it was observed that the progression of COPD was strongly associated with the parenchymal infiltration by innate and adaptive inflammatory immune cells forming an ectopic lymphoid follicle containing a germinal center. The presence of the lymphoid follicle was coupled to a remodeling process that thickened the distal small airway walls (16). This result strongly suggests the potential pathological role of the ectopic lymphoid follicles in COPD.

In an effort to identify novel genes involved in the pathogenesis of asthma, researchers have used DNA microarray technology to profile genes that are differentially expressed in animal models of asthma (17,18). Microarray technology is a powerful tool since it enables analysis of the expression of thousands of genes simultaneously and can also be automated allowing for a high-throughput format. In multifactorial diseases, such as asthma, microarray results can provide a gene expression profile which can prove very useful in designing new therapeutics. Also, it can prove very powerful in identifying novel genes and annotating genes of unknown function (19).

CXCL13 (a.k.a BLC (B cell homing chemokine) or BCA-1 (B cell attracting chemokine 1) or Angie 2)) is a chemotactic factor that most strongly and selectively attracts B cells. It also promotes migration of certain T cells and macrophages through the receptor CXCR5 (20). CXCL13 is expressed in the follicles of Peyer's patches, spleen and lymph nodes, and is believed to be important in follicle development and homeostasis (21).

It has been observed for years that in the sites of chronic inflammation, the arrangement of the inflammatory infiltrate (T, B and stromal cells) shares many architectural features with lymphoid tissue, which forms the so called ectopic lymphoid follicles (21). In addition, extopic high production of CXCL13 is associated with lymphocyte accumulation and ectopic lymphoid follicle formation in chronic inflammatory diseases, such as rheumatoid arthritis (21), Sjogren's syndrome (22), various forms of lupus such as systemic lupus erythematosus (23, 24), ulcerative colitis (25, 26), multiple sclerosis (27-29), type I diabetes (30-32) and autoimmune thyroid diseases (33, 34). Although the exact pathogenic role of the ectopic lymphoid follicles is not clear, evidence suggests its importance in the switch from acute, resolving to chronic, persistent inflammation by allowing lymphocytes to accumulate in the local inflamed tissue (35). Therefore, disrupting or eliminating the ectopic lymphoid follicles would provide a novel therapeutic approach to control chronic inflammatory diseases. CXCL13 is an ideal therapeutic target due to its high expression levels in the ectopic lymphoid follicles and its role in maintaining their microstructure and attracting B cells.

Systemic lupus erythematosus (SLE or lupus) is a chronic autoimmune disease that is potentially debilitating and sometimes fatal as the immune system attacks the body's cells and tissue, resulting in inflammation and tissue damage. SLE can affect any part of the body, but most often harms the heart, joints, skin, lungs, blood vessels, liver, kidneys and nervous system.

The CXCL13 gene (GenBank Accession No. NM_006419, SEQ ID NO:1) resides on human chromosome 4q21. CXCL13 belongs to the CXC chemokine family. CXCL13 is critical for lyphoid organ formation/development, B cell follicle formation, and B cell recruitment. It is highly produced ectopically in the inflamed tissues of multiple chronic inflammatory diseases, and is believed to play an important role in maintaining local B and T cell activation and inflammation.

Gene expression can be modulated in several different ways, including by the use of siRNAs, shRNAs, antisense molecules and DNAzymes. SiRNAs and shRNAs both work via the RNAi pathway and have been successfully used to suppress the expression of genes. RNAi was first discovered in worms and the phenomenon of gene silencing related to dsRNA was first reported in plants by Fire and Mello and is thought to be a way for plant cells to combat infection with RNA viruses. In this pathway, the long dsRNA viral product is processed into smaller fragments of 21-25 bp in length by a DICER-like enzyme and then the double-stranded molecule is unwound and loaded into the RNA induced silencing complex (RISC). A similar pathway has been identified in mammalian cells with the notable difference that the dsRNA molecules must be smaller than 30 bp in length in order to avoid the induction of the so-called interferon response, which is not gene specific and leads to the global shut down of protein synthesis in the cell.

Synthetic siRNAs can be designed to specifically target one gene and they can easily be delivered to cells in vitro or in vivo. ShRNAs are the DNA equivalents of siRNA molecules and have the advantage of being incorporated into the cells' genome and then being replicated during every mitotic cycle.

DNAzymes have also been used to modulate gene expression. DNAzymes are catalytic DNA molecules that cleave single-stranded RNA. They are highly selective for the target RNA sequence and as such can be used to down-regulate specific genes through targeting of the messenger RNA.

Accordingly, there is a need to identify and characterize new methods for diagnosing and treatment related to CXCL13 for pulmonary disorders, such as asthma, and related diseases and conditions. Additionally, there is a need to identify and characterize new methods for treating disorders such as systemic lupus erythematosus.

SUMMARY OF THE INVENTION

The present invention relates to agonists and/or antagonists of CXCL13 or its receptor, CXCR5, and/or one or both of their activities (hereinafter "CXCL13 antagonists") and a method of using CXCL13 antagonists, including antibodies directed toward CXCL13, and specified portions or variants thereof specific for at least one CXCL13 protein or fragment thereof, to treat pulmonary-related disorders. These CXCL13 antagonists can be administered along with TNFα antagonists, such TNFα antibodies, e.g., infliximab et al. A CXCL13 antagonist, such as a monoclonal antibody, inhibits local B and T cell recruitment and subsequent activation to provide a novel strategy to control chronic immune mediated inflammatory diseases.

In one embodiment, the CXCL13 antagonist is an antibody that specifically binds to CXCL13 or its receptor. A particular advantage of such antibodies is that they are capable of binding CXCL13 or its receptor in a manner that prevents its action. The method of the present invention thus employs antibodies having the desirable neutralizing property which makes them ideally suited for therapeutic and preventative treatment of disease states associated with various pulmonary-related disorders in human or nonhuman patients. Accordingly, the present invention is directed to a method of treating a pulmonary-related disease or condition in a patient in need of such treatment which comprises administering to the patient an amount of a neutralizing CXCL13 antibody to inhibit the pulmonary-related disease or condition.

In another aspect, the invention provides methods for modulating activity of CXCL13 or its receptor comprising contacting a cell with an agent (e.g., antagonist or agonist) that modulates (inhibits or enhances) the activity or expression of CXCL13 or its receptor such that activity or expression in the cell is modulated. In a preferred embodiment, the agent is an antibody that specifically binds to CXCL13 or its receptor. In other embodiments, the modulator is a peptide, peptidomimetic, or other small molecule.

In another embodiment, the present invention is directed to a method of treating a pulmonary-related disease or condition in a patient in need of such treatment, which comprises administering to the patient an amount of a neutralizing CXCL13 antibody or other antagonist along with one or more TNFα antagonists to inhibit the pulmonary-related disease or condition.

The present invention also provides methods of treating a subject having a pulmonary or related disorder wherein the disorder can be ameliorated by modulating the amount or activity of CXCL13. The present invention also provides methods of treating a subject having a disorder characterized by aberrant activity of CXCL13 or its encoding polynucleotide by administering to the subject an agent that is a modulator of the activity of CXCL13 or a modulator of the expression of CXCL13.

In one embodiment, the modulator is a polypeptide or small molecule compound. In another embodiment, the modulator is a polynucleotide. In a particular embodiment, the CXCL13 antagonist is an siRNA molecule, an shRNA molecule, or a DNAzyme capable of preventing the production of CXCL13 by cells.

Another aspect of the invention is a method for treating an animal with systemic lupus erythematosus comprising providing an antagonist of CXCL-13 to the animal, and providing an antagonist of TNF-alpha to the animal; wherein each antagonist is provided in an amount effective to cause a decrease in a symptom of systemic lupus erythematosus in the animal. In one embodiment of this method the antagonist of CXCL-13 is a CXCL-13 binding antibody or CXCL-13 binding fragment of an antibody and the antagonist of TNFα is a TNFα binding antibody or a TNFα binding fragment of an antibody.

In another embodiment of this method the animal is a mammal. In another embodiment of this method the mammal is a human. In another embodiment of this method the amount of each antibody or binding fragment of an antibody provided is from about 25 mg per kg body weight of the animal to about 40 mg per kg body weight of the animal. In another embodiment of this method the symptom of systemic lupus erythematosus is the number of periarterial lymphocyte infiltrate foci identified by examination of the kidney tissues. In another embodiment of this method the symptom of systemic lupus erythematosus is the ratio of total urine protein to total urine creatinine. In another embodiment of this method the antagonist of CXCL-13 is a CXCL-13 binding antibody or CXCL-13 binding fragment of an antibody and the antagonist of TNFα is a TNFα binding antibody or a TNFα binding fragment of an antibody. In another embodiment of this method the antagonist of CXCL-13 is a CXCL-13 binding antibody or CXCL-13 binding fragment of an antibody and the antagonist of TNFα is the TNFα binding antibody infliximab.

The present invention further provides any invention described herein.

DETAILED DESCRIPTION OF THE INVENTION

Definitions

Figure 1:
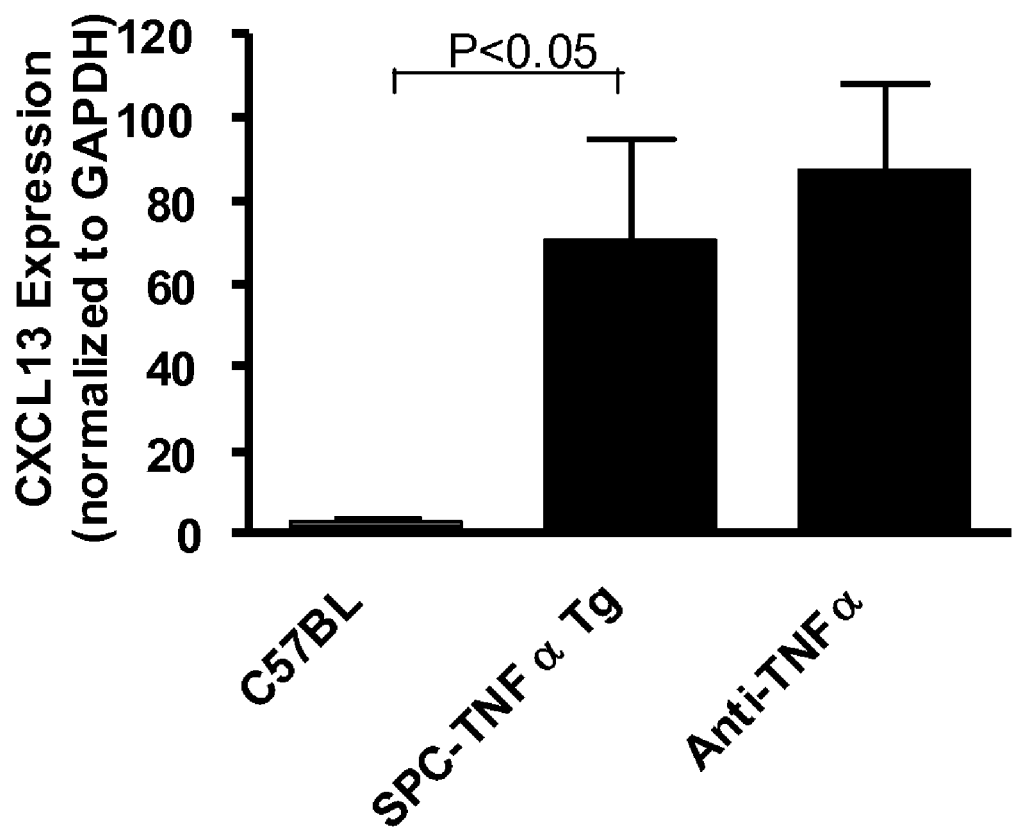
FIG. 1 shows that CXCL13 mRNA transcript levels are elevated in diseased lung tissues.

The following definitions are set forth to illustrate and define the meaning and scope of various terms used to describe the invention herein.

An "activity," a biological activity, and a functional activity of a polypeptide refers to an activity exerted by CXCL13 or its receptor in response to its specific interaction with another protein or molecule as determined in vivo, in situ, or in vitro, according to standard techniques. Such activities can be a direct activity, such as an association with or an enzymatic activity on a second protein, or an indirect activity, such as a cellular process mediated by interaction of the protein with a second protein or a series of interactions as in intracellular signaling or the coagulation cascade.

An "antibody" includes any polypeptide or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion, fragment or variant thereof. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies, single domain antibodies, and fragments thereof. For example, antibody fragments include, but are not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, et al., eds., Current Protocols in Immunology, John Wiley & Sons, Inc., NY (1994-2001); Colligan et al., Current Protocols in Polypeptide Science, John Wiley & Sons, NY (1997-2001)).

"Chimeric" or "fusion" molecules are nucleic acids or polypeptides that are created by combining, for example, one or more CXCL13 antagonists (or their parts) with additional nucleic acid sequence(s). Such combined sequences may be introduced into an appropriate vector and expressed to give rise to a chimeric or fusion polypeptide.

"Complement of" or "complementary to" a nucleic acid sequence of the invention refers to a polynucleotide molecule having a complementary base sequence and reverse orientation as compared to a first polynucleotide.

"Fragment" is a variant polypeptide having an amino acid sequence that is entirely the same as part but not all of any amino acid sequence of a CXCL13 antagonist or a variant polynucleotide having a nucleic acid sequence that is entirely the same as part but not all of any nucleic acid sequence of any CXCL13 antagonist polynucleotide. Fragments can include, e.g., truncation polypeptides, or variants thereof, such as a continuous series of residues that includes a heterologous amino- and/or carboxy-terminal amino acid sequence. Degradation forms of the CXCL13 antagonists produced by or in a host cell are also included. Other exemplary fragments are characterized by structural or functional attributes, such as fragments that comprise alpha-helix or alpha-helix forming regions, beta-sheet or beta-sheet forming regions, turn or turn-forming regions, coil or coil-forming regions, hydrophilic regions, hydrophobic regions, alpha-amphipathic regions, beta-amphipathic regions, flexible regions, surface-forming regions, substrate binding regions, extracellular regions, and high antigenic index regions.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215: 403-410 (1990). The well-known Smith Waterman algorithm may also be used to determine identity.

Preferred parameters for polypeptide sequence comparison include the following:

(1) Algorithm: Needleman and Wunsch, J. Mol Biol. 48:443-453 (1970) Comparison matrix: BLOSSUM62 from Hentikoff and Hentikoff, Proc. Natl. Acad. Sci, USA. 89:10915-10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide sequence comparisons (along with no penalty for end gaps).

Preferred parameters for polynucleotide comparison include the following:
(1) Algorithm: Needleman and Wunsch, J. Mol Biol. 48:443-453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid sequence comparisons.

By way of example, a polynucleotide sequence may be identical to a sequence, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the sequence by the numerical percent of the respective percent identity (divided by 100) and subtracting that product from the total number of nucleotides in the sequence, or:

$n_n \le x_n - (x_n \cdot y)$, wherein $n_n$ is the number of nucleotide alterations, $x_n$ is the total number of nucleotides in the sequence, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting from $x_n$.

Alterations of a polynucleotide sequence encoding the sequence may create nonsense, missense or frameshift mutations in this coding sequence and thereby alter the polypeptide encoded by the polynucleotide following such alterations. Similarly, a polypeptide sequence may be identical to the reference sequence, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the sequence by the numerical percent of the respective percent identity (divided by 100) and then subtracting that product from the total number of amino acids in the sequence, or:

$n_a \le x_a - (x_a \cdot y)$, wherein $n_a$ is the number of amino acid alterations, $x_a$ is the total number of amino acids in the sequence, and y is, for instance 0.70 for 70%, 0.80 for 80%, 0.85 for 85% etc., and wherein any non-integer produce of $x_a$ and y is rounded down to the nearest integer prior to subtracting it from $x_a$.

"Nucleic acids" are polymers of nucleotides, wherein a nucleotide comprises a base linked to a sugar which sugars are in turn linked one to another by an interceding at least bivalent molecule, such as phosphoric acid. In naturally occurring nucleic acids, the sugar is either 2'-deoxyribose (DNA) or ribose (RNA). Unnatural poly- or oliogonucleotides contain modified bases, sugars, or linking molecules, but are generally understood to mimic the complementary nature of the naturally occurring nucleic acids after which they are designed. An example of an unnatural oligonucleotide is an antisense molecule composition that has a phosphorothioate backbone. An "oligonucleotide" generally refers to a nucleic acid molecule having less than 30 nucleotides.

A "polypeptide" is a polymer of amino acid residues joined by peptide bonds, and a peptide generally refers to amino acid polymers of 12 or less residues. Peptide bonds can be produced naturally as directed by the nucleic acid template or synthetically by methods well known in the art.

A "protein" is a macromolecule comprising one or more polypeptide chains. A protein may further comprise substituent groups attached to the side groups of the amino acids not involved in formation of the peptide bonds. Typically, proteins formed by eukaryotic cell expression also contain carbohydrates. Proteins are defined herein in terms of their amino acid sequence or backbone and substituents are not specified, whether known or not.

The term "receptor" denotes a molecule having the ability to affect biological activity, in e.g., a cell, as a result of interaction with a specific ligand or binding partner. Cell membrane bound receptors are characterized by an extracellular ligand-binding domain, one or more membrane spanning or transmembrane domains, and an intracellular effector domain that is typically involved in signal transduction. Ligand binding to cell membrane receptors causes changes in the extracellular domain that are communicated across the cell membrane, direct or indirect interaction with one or more intracellular proteins, and alters cellular properties, such as enzyme activity, cell shape, or gene expression profile. Receptors may also be untethered to the cell surface and may be cytosolic, nuclear, or released from the cell altogether. Non-cell associated receptors are termed soluble receptors.

All publications or patents cited herein are entirely incorporated herein by reference, whether or not specifically designated accordingly, as they show the state of the art at the time of the present invention and/or provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY (1987-2001); Sambrook, et al., Molecular Cloning: A Laboratory Manual, 2nd Edition, Cold Spring Harbor, NY (1989); Harlow and Lane, antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY (1997-2001).

Biological Function of CXCL13

Novel expression and novel function of CXCL13, and its biological function in lymphoid organ formation/development, B cell follicle formation, and B cell recruitment have been identified in various human diseases and animal models. For the first time, ectopic expression has been linked with lymphoid follical formation associated with pulmonary diseases, particularly but not limited to, COPD.

CXCL13 compositions may comprise one or more protein isoforms, immunogenic portions thereof, or polynucleotides that encode such portions. Alternatively, a therapeutic composition may comprise a cell that expresses CXCL13 protein, or a T cell that is specific for cells expressing a polypeptide encoded by the gene, or other type of agonists; and antagonistic agents, such as neutralizing monoclonal antibodies (mAb), nucleic acid-based therapies, or small molecule compounds to any portion of CXCL13 DNA, RNA or protein. These compositions may be used, for example, for the prevention and treatment of a range of immue-mediated inflammatory diseases. Diagnostic and prognostic methods based on detecting CXCL13 protein, or mRNA encoding such a protein, in a sample are disclosed.

CXCL13 and its receptor proteins, polypeptides, and nucleic acid molecules encoding them comprise a family of molecules having certain conserved structural and functional features. Each of these molecules is included in the definition of CXCL13. As used herein, the term "family" is intended to mean two or more proteins or nucleic acid molecules having a common or similar domain structure and having sufficient amino acid or nucleotide sequence identity as defined herein. Family members can be from either the same or a different species. For example, a family can comprise two or more proteins of human origin, or can comprise one or more proteins of human origin and one or more of non-human origin.

A domain that may be present in CXCL13 proteins is a signal sequence. As used herein, a "signal sequence" includes a peptide of at least about 10 amino acid residues in length which occurs at the amino terminus of membrane-bound proteins and which contains at least about 45% hydrophobic amino acid residues, such as alanine, leucine, isoleucine, phenylalanine, proline, tyrosine, tryptophan, or valine. In a preferred embodiment, a signal sequence contains at least about 10 to 35 amino acid residues, preferably about 10 to 20 amino acid residues, and has at least about 35-60%, more preferably 40-50%, and more preferably at least about 45% hydrophobic residues. A signal sequence serves to direct a protein containing such a sequence to a lipid bilayer. Thus, in one embodiment, a CXCL13 protein may contain a signal sequence. The signal sequence is cleaved during processing of the mature protein.

CXCL13 proteins include an extracellular domain. As used herein, an "extracellular domain" refers to a portion of a protein that is localized to the non-cytoplasmic side of a lipid bilayer of a cell when a nucleic acid encoding the protein is expressed in the cell.

In addition, a CXCL13 protein includes a transmembrane domain. As used herein, a "transmembrane domain" refers to an amino acid sequence which is at least about 15 amino acid residues in length and which contains at least about 65-70% hydrophobic amino acid residues such as alanine, leucine, phenylalanine, protein, tyrosine, tryptophan, or valine (Erik, et al. Proc. of Sixth Int. Conf. on Intelligent Systems for Molecular Biology, p 175-182). In a preferred embodiment, a transmembrane domain contains about 15-30 amino acid residues, preferably about 20-25 amino acid residues, and has at least about 60-80%, more preferably 65-75%, and more preferably at least about 70% hydrophobic residues.

CXCL13 proteins have a cytoplasmic domain, particularly including proteins having a carboxyl-terminal cytoplasmic domain. As used herein, a "cytoplasmic domain" refers to a portion of a protein that is localized to the cytoplasmic side of a lipid bilayer of a cell when a nucleic acid encoding the protein is expressed in the cell. CXCL13 proteins typically comprise a variety of potential post-translational modification sites (often within an extracellular domain).

CXCL13 Antagonists

As used herein, the term "CXCL13 antagonists" refers to substances which inhibit or neutralize the biologic activity of CXCL13 or its receptor, CXCR5. Such antagonists accomplish this effect in a variety of ways. One class of CXCL13 antagonists will bind to the CXCL13 protein with sufficient affinity and specificity to neutralize the biologic effects of CXCL13. Included in this class of molecules are antibodies and antibody fragments (such as, for example, F(ab) or F(ab')$_2$ molecules). Another class of CXCL13 antagonists comprises fragments of the CXCL13 protein, muteins or small organic molecules, i.e., peptidomimetics, that will bind to the CXCL13 or CXCL13 binding partners, thereby inhibiting the biologic activity of CXCL13. The CXCL13 antagonist may be of any of these classes as long as it is a substance that inhibits CXCL13 biologic activity. CXCL13 antagonists include CXCL13 antibody, CXCL13 receptor antibody, modified CXCL13, and partial peptides of the CXCL13. Another class of CXCL13 antagonists includes siRNAs, shRNAs, antisense molecules and DNAzymes targeting the CXCL13 gene sequence as known in the art are disclosed herein.

Accordingly, as used herein, a "CXCL13 antibody," "anti-CXCL13 antibody," "anti-CXCL13 antibody portion," or "anti-CXCL13 antibody fragment" and/or "anti-CXCL13 antibody variant" and the like include any protein or polypeptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of a CXCL13 binding protein derived from a CXCL13 protein or peptide, which can be incorporated into an antibody for use in the present invention. Such antibody optionally further affects a specific ligand, such as, but not limited to, where such antibody modulates, decreases, increases, antagonizes, agonizes, mitigates, alleviates, blocks, inhibits, abrogates and/or interferes with CXCL13 activity, in vitro, in situ and/or in vivo. As a non-limiting example, a suitable anti-CXCL13 antibody, specified portion or variant of the present invention can bind at least one CXCL13 protein or peptide, or specified portions, variants or domains thereof. A suitable anti-CXCL13 antibody, specified portion, or variant affects CXCL13 function in a variety of ways, such as, but not limited to, RNA, DNA or protein synthesis, CXCL13 release, CXCL13 signaling, CXCL13 binding, CXCL13 production and/or synthesis.

Antibodies can include one or more of at least one CDR, at least one variable region, at least one constant region, at least one heavy chain (e.g., g1, g2, g3, g4, m, a1, a2, d, e), at least one light chain (e.g., k and l), or any portion or fragment thereof, and can further comprise interchain and intrachain disulfide bonds, hinge regions, glycosylation sites that can be separated by a hinge region, as well as heavy chains and light chains. Light chains typically have a molecular weight of about 25 Kd and heavy chains typically range from about 50K-77 Kd. Light chains can exist in two distinct forms or isotypes, kappa (k) and lambda (l), which can combine with any of the heavy chain types. All light chains have at least one variable region and at least one constant region. The IgG antibody is considered a typical antibody structure and has two intrachain disulfide bonds in the light chain (one in the variable region and one in the constant region), with four in the heavy chain, and such bond encompassing a peptide loop of about 60-70 amino acids comprising a "domain" of about 110 amino acids in the chain. IgG antibodies can be characterized into four classes, IgG1, IgG2, IgG3 and IgG4. Each immunoglobulin class has a different set of functions. Table 1 summarizes the physicochemical properties of each of the immunoglobulin classes and subclasses.

TABLE 1

| Property | IgG1 | IgG2 | IgG3 | IgG4 | IgM | IgA1 | IgA2 | SigA | IgD | IgE |
|---|---|---|---|---|---|---|---|---|---|---|
| Heavy Chain | γ1 | γ1 | γ1 | γ1 | μ | α1 | α2 | α1/α2 | δ | e |
| Mean Serum conc. (mg/ml) | 9 | 3 | 1 | 0.5 | 1.5 | 3.0 | 0.5 | 0.05 | 0.03 | 0.00005 |
| Sedimentation constant | 7s | 7s | 7s | 7s | 19s | 7s | 7s | 11s | 7s | 8s |
| Mol. Wt. ($\times 10^3$) | 146 | 146 | 170 | 146 | 970 | 160 | 160 | 385 | 184 | 188 |
| Half Life (days) | 21 | 20 | 7 | 21 | 10 | 6 | 6 | ? | 3 | 2 |
| % intravascular distribution | 45 | 45 | 45 | 45 | 80 | 42 | 42 | Trace | 75 | 50 |
| Carbohydrate (%) | 2-3 | 2-3 | 2-3 | 2-3 | 12 | 7-11 | 7-11 | 7-11 | 9-14 | 12 |

Table 2 summarizes non-limiting examples of antibody effector functions for human antibody classes and subclasses.

TABLE 2

| Effector function | IgG1 | IgG2 | IgG3 | IgG4 | IgM | IgA | IgD | IgE |
|---|---|---|---|---|---|---|---|---|
| Complement fixation | + | +/− | ++ | − | ++ | − | − | − |
| Placental transfer | + | +/− | + | + | − | − | − | − |
| Binding to Staph A | +++ | +++ | − | +++ | − | − | − | − |
| Binding to Strep G | +++ | +++ | +++ | +++ | − | − | − | − |

+++ = very high;
++ = high;
+ = moderate;
+/− = minimal;
− = none;
? = questionable Accordingly, the type of antibody or fragment thereof can be selected for use according to the present invention based on the desired characteristics and functions that are desired for a particular therapeutic or diagnostic use, such as but not limited to, serum half life, intravascular distribution, complement fixation, etc.

An isolated CXCL13 polypeptide, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a CXCL13 protein comprises at least 8 (preferably 10, 15, 20, or 30 or more) amino acid residues and encompasses an epitope of the protein such that an antibody raised against the peptide forms a specific immune complex with the protein.

An immunogen typically is used to prepare antibodies by immunizing a suitable (i.e., immunocompetent) subject, such as a rabbit, goat, mouse, or other mammal or vertebrate. An appropriate immunogenic preparation can contain, for example, recombinantly expressed or chemically synthesized polypeptide. The preparation can further include an adjuvant, such as Freund's complete or incomplete adjuvant, or a similar immunostimulatory agent.

Antibody-producing cells can be obtained from the peripheral blood or, preferably, the spleen or lymph nodes of humans or other suitable animals that have been immunized with the immunogen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells that produce antibodies with the desired specificity can be selected by a suitable assay (e.g., ELISA).

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like), or heteromyelomas, fusion products thereof, or any cell or fusion cell derived therefrom, or any other suitable cell line as known in the art (see, e.g., www.atcc.org, www.lifetech.com, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Other suitable methods of producing or isolating antibodies of the requisite specificity can be used, including, but not limited to, methods that select recombinant antibody from a peptide or polypeptide library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, Calif.; Ixsys. See, e.g., EP Publication No. 368,684; PCT/GB91/01134; PCT/GB92/01755; PCT/GB92/002240; PCT/GB92/00883; PCT/GB93/

00605; U.S. Pat. No. 5,962,255; PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); EP 614 989 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or polypeptides—U.S. Pat. Nos. 5,723,323, 5,763,192, 5,814,476, 5,817,483, 5,824,514, and 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (Nov. 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is not human, e.g., but not limited to, mouse, rat, rabbit, non-human primate or other mammal. The human amino acid residues are often referred to as "import" residues, which are typically taken from an "import" variable, constant or other domain of a known human sequence. Known human Ig sequences are disclosed, e.g., www. ncbi.nlm.nih.gov/entrez/query.fcgi; www. ncbi.nih.gov/igblast; www. atcc.org/phage/hdb.html; www. mrc-cpe.cam.ac.uk/ALIGNMENTS.php; www. kabatdatabase.com/top.html; ftp.ncbi.nih.gov/repository/kabat; www. sciquest.com; www. abcam.com; www. antibodyresource.com/onlinecomp.html; www. publiciastate.edu/~pedro/research_tools.html; www. whfreeman.com/immunology/CH05/kuby05.htm; www. hhmi.org/grants/lectures/1996/vlab; www. path.cam.ac.uk/~mrc7/mikeimages.html; mcb.harvard.edu/BioLinks/Immunology.html; www. immunologylink.com; pathbox.wustl.edu/~hcenter/index.html; www. appliedbiosystems.com; www. nal.usda.gov/awic/pubs/antibody; www. m.ehimeu.ac.jp/~yasuhito/Elisa.html; www. biodesign.com; www. cancerresearchuk.org; www. biotech.ufl.edu; www. isacnet.org; baserv.uci.kun.nl/~jraats/links1.html; www. recab.uni-hd.de/immuno.bme.nwu.edu; www. mrc-cpe.cam.ac.uk; www. ibt.unam.mx/virN_mice.html; http://www.bioinf.org.uk/abs; antibody.bath.ac.uk; www. unizh.ch; www. cryst.bbk.ac.uk/~ubcg07s; www. nimr.mrc.ac.uk/CC/ccaewg/ccaewg.html; www. path.cam.ac.uk/~mrc7/humanisation/TAHHP.html; www. ibt.unam.mx/vir/structure/sta_aim.html; www. biosci.missouri.edu/smithgp/index.html; www. jerini.de; Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally, part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to, those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Clothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567; PCT/:US98/16280; US96/18978; US91/09630; US91/05939; US94/01234; GB89/01334; GB91/01134; GB92/01755; WO90/14443; WO90/14424; and WO90/14430; EP 229246; each entirely incorporated herein by reference, including references cited therein.

The CXCL13 antibody can also be optionally generated by immunization of a transgenic animal (e.g., mouse, rat, hamster, non-human primate, and the like) capable of producing a repertoire of human antibodies, as described herein and/or as known in the art. Cells that produce a human CXCL13 antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. US. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., *Int. Immunol.* 6(4)579-591 (1994), Green et al, *Nature Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7): 845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Antibodies of the present invention can also be prepared in milk by administering at least one anti-CXCL13 antibody encoding nucleic acid to transgenic animals or mammals, such as goats, cows, horses, sheep, and the like, that produce antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference. Antibodies of the present invention can additionally be prepared using at least one CXCL13 antibody encoding nucleic acid to provide transgenic plants and cultured plant cells (e.g., but not limited to, tobacco and maize) that produce such antibodies, specified portions or variants in the plant parts or in cells cultured therefrom.

The antibodies of the invention can bind human CXCL13 with a wide range of affinities ($K_D$). In a preferred embodiment, at least one human mAb of the present invention can optionally bind human CXCL13 with high affinity. For example, a human mAb can bind human CXCL13 with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

A CXCL13 antagonist (e.g., monoclonal antibody) can be used to isolate the CXCL13 polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to mammalian CXCL13. For example, antibody fragments capable of binding to CXCL13 or portions thereof, including, but not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')2 heavy chain portion can be designed to include DNA sequences encoding the $C_H1$ domain and/or hinge region of the heavy chain. The various portions of antibodies can be joined together chemically by conventional techniques, or can be prepared as a contiguous protein using genetic engineering techniques.

The anti-CXCL13 antibody may be a primate, rodent, or human antibody or a chimeric or humanized antibody. As used herein, the term "human antibody" refers to an antibody in which substantially every part of the protein (e.g., CDR, framework, CL, CH domains (e.g., $C_H1$, $C_H2$, $C_H3$), hinge, (VL, VH)) is substantially non-immunogenic in humans, with only minor sequence changes or variations, and/or is engineered to, derived from, or contains known human antibody components. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies of the invention can include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as 2 to about 8 glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably human or humanized, antibodies that have binding specificities for at least two different antigens. In the present case, one of the binding specificities is for at least one CXCL13 protein, the other one is for any other antigen, e.g., CXCL13 receptor or TNFα. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-CXCL13 antibodies useful in the methods and compositions of the present invention can optionally be characterized by high affinity binding to CXCL13 and optionally and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344:1125-1127 (1994), entirely incorporated herein by reference).

Suitable antibodies include those that compete for binding to human CXCL13 with monoclonal antibodies that block CXCL13 activation.

CXCL13 Antagonists in the Form of siRNA, shRNA, Antisense, Ribozymes, and DNAzymes A therapeutic targeting the inducer of the CXCL13 may provide better chances of success. Gene expression can be modulated in several different ways including by the use of siRNAs, shRNAs, antisense molecules, ribozymes, and DNAzymes. Synthetic siRNAs, shRNAs, ribozymes, and DNAzymes can be designed to specifically target one or more genes and they can easily be delivered to cells in vitro or in vivo.

The present invention encompasses antisense nucleic acid molecules, i.e., molecules that are complementary to a sense nucleic acid encoding a CXCL13 polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a CXCL13 polypeptide. The non-coding regions ("5' and 3' untranslated regions") are the 5' and 3' sequences that flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives, peptide nucleic acids (PNAs), and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected CXCL13 polypeptide to thereby inhibit expression, e.g., by inhibiting transcription and/or translation. The hybridization can be by conventional nucleotide complementarity to form a stable duplex or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then be administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The invention also encompasses ribozymes. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach (1988) *Nature* 334:585-591) can be used to catalytically cleave mRNA transcripts to thereby inhibit translation of the protein encoded by the mRNA. A ribozyme having specificity for a nucleic acid molecule encoding a CXCL13 polypeptide can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in Cech et al., U.S. Pat. No. 4,987,071; and Cech et al., U.S. Pat. No. 5,116,742. Alternatively, an mRNA encoding a CXCL13 polypeptide can be used to select a catalytic RNA having a specific ribonuclease activity from a pool of RNA molecules. See, e.g., Haselhoff and Gerlach supra; Bartel and Szostak (1993) *Science* 261:1411-1418.

The invention also encompasses ribonucleic acid molecules which are complementary, antisense, double stranded homologues, siRNA, or are sequence specific single-stranded RNAs which form short hairpin structures, shRNA (collectively, interfering RNA), that can be used to down-modulate specific gene expression, in this case, CXCL13, and therefore to inhibit protein expression and to elucidate their respective biological functions. (Fire, A., et al. (1998) Nature 391: 806-811; Paddison, P. J. et al. (2002) Genes Develop 16:948-958).

The invention further encompasses DNAzymes that are capable of cleaving either RNA (Breaker and Joyce, 1994; Santoro and Joyce, 1997) or DNA (Carmi et al., 1996) molecules. The rate of catalytic cleavage of such nucleic acid enzymes is dependent on the presence and concentration of divalent metal ions such as $Ba^{2+}$, $Sr^{2+}$, $Mg^{2+}$, $Ca^{2+}$, $Ni^{2+}$, $Co^{2+}$, $Mn^{2+}$, $Zn^{2+}$, and $Pb^{2+}$ (Santoro and Joyce, 1998; Brown et al., 2003).

Catalytic DNAzymes, such as the 10:23 and 8:17 DNAzymes, have multiple domains. They have a conserved catalytic domain (catalytic core) flanked by two non-conserved substrate binding domains (hybridizing arms), which are regions of sequence that specifically bind to the substrate. The 10:23 and 8:17 DNAzymes are capable of cleaving nucleic acid substrates at specific RNA phosphodiester bonds (Santoro and Joyce, 1997). The 10:23 DNAzyme has a catalytic domain of 15 deoxynucleotides flanked by two substrate-recognition arms. The 8:17 DNAzyme is of similar size.

A catalytic nucleic acid can cleave a nucleic acid substrate with a target sequence that meets minimum requirements. The substrate sequence must be substantially complementary to the hybridizing arms of the catalytic nucleic acid, and the substrate must contain a specific sequence at the site of cleavage. Specific sequence requirements at the cleavage site include, for example, a purine:pyrimidine ribonucleotide sequence for cleavage by the 10:23 DNAzyme (Santoro and Joyce, 1997).

In various embodiments, the nucleic acid molecules of the invention can be modified at the base moiety, sugar moiety, or phosphate backbone to improve, e.g., the stability, hybridization, or solubility of the molecule. For example, the nucleotide analogs as described above can be substituted for the naturally occurring nucleotides.

In another example, the deoxyribose phosphate backbone of the nucleic acids can be modified to generate peptide nucleic acids (see Hyrup et al. (1996) *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93: 14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) *Proc. Natl. Acad. Sci. USA* 93: 14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17): 3357-63. For example, a DNA chain can be synthesized on a solid support using standard phosphoramidite coupling chemistry and modified nucleoside analogs. Compounds, such as 5'-(4-methoxytrityl)amino-5'-deoxy-thymidine phosphoramidite, can be used as a link between the PNA and the 5' end of DNA (Mag et al. (1989) *Nucleic Acids Res.* 17:5973-88). PNA monomers are then coupled in a step-wise manner to produce a chimeric molecule with a 5' PNA segment and a 3' DNA segment (Finn et al. (1996) *Nucleic Acids Res.* 24(17):3357-63). Alternatively, chimeric molecules can be synthesized with a 5' DNA segment and a 3' PNA segment (Peterser et al. (1975) *Bioorganic Med. Chem. Lett.* 5:1119-11124).

In other embodiments, the oligonucleotide can include other appended groups, such as peptides (e.g., for targeting host cell receptors in vivo), or agents facilitating transport across the cell membrane (see, e.g., Letsinger et al. (1989)

*Proc. Natl. Acad. Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958-976) or intercalating agents (see, e.g., Zon (1988) *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Proteins

The invention also provides chimeric or fusion proteins. As used herein, a "chimeric protein" or "fusion protein" comprises all or part (preferably biologically active) of a CXCL13 polypeptide operably linked to a heterologous polypeptide (i.e., a polypeptide other than the same CXCL13 polypeptide). Within the fusion protein, the term "operably linked" is intended to indicate that the CXCL13 polypeptide and the heterologous polypeptide are fused in-frame to each other. The heterologous polypeptide can be fused to the amino-terminus or the carboxyl-terminus of the CXCL13 polypeptide. In another embodiment, a CXCL13 polypeptide or a domain or active fragment thereof can be fused with a heterologous protein sequence or fragment thereof to form a chimeric protein, where the polypeptides, domains or fragments are not fused end to end but are interposed within the heterologous protein framework.

One useful fusion protein is a GST fusion protein in which the CXCL13 polypeptide is fused to the carboxyl terminus of GST sequences. Such fusion proteins can facilitate the purification of a recombinant CXCL13 polypeptide.

In another embodiment, the fusion protein contains a heterologous signal sequence at its amino terminus. For example, the native signal sequence of a CXCL13 polypeptide can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a CXCL13 polypeptide is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a CXCL13 polypeptide. Inhibition of ligand/receptor interaction can be useful therapeutically, both for treating proliferative and differentiative disorders and for modulating (e.g., promoting or inhibiting) cell survival. A preferred embodiment of an immunoglobulin chimeric protein is a $C_H1$ domain-deleted immunoglobulin or "mimetibody" having an active polypeptide fragment interposed within a modified framework region as taught in co-pending application PCT WO/04002417. Moreover, the immunoglobulin fusion proteins of the invention can be used as immunogens to produce antibodies directed against a CXCL13 polypeptide in a subject, to purify ligands and in screening assays to identify molecules that inhibit the interaction of receptors with ligands.

Chimeric and fusion proteins of the invention can be produced by standard recombinant DNA techniques. In another embodiment, the fusion gene can be synthesized by conventional techniques, including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a CXCL13 polypeptide can be cloned into such an expression vector such that the fusion moiety is linked in-frame to the CXCL13 polypeptide.

A signal sequence of a CXCL13 polypeptide can be used to facilitate secretion and isolation of the secreted protein or other proteins of interest. Signal sequences are typically characterized by a core of hydrophobic amino acids that are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector to a protein of interest, such as a protein that is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence that facilitates purification, such as with a GST domain.

In another embodiment, the signal sequences of the present invention can be used to identify regulatory sequences, e.g., promoters, enhancers, and/or repressors. Since signal sequences are the most amino-terminal sequences of a peptide, the nucleic acids flanking the signal sequence on its amino-terminal side are likely regulatory sequences that affect transcription. Thus, a nucleotide sequence that encodes all or a portion of a signal sequence can be used as a probe to identify and isolate signal sequences and their flanking regions, and these flanking regions can be studied to identify regulatory elements therein.

The present invention also pertains to variants of the CXCL13 polypeptides and can include one or more amino acid substitutions, deletions or additions, either from natural mutations or human manipulation, as specified herein. Such mutations or substitutions can include muteins, whose mutations can be significant enough to alter the properties of the peptide without altering the biological activity of the peptide to inhibit the binding of human CXCL13 to its ligand. Of course, the number of amino acid substitutions a skilled artisan would make depends on many factors, including those described above. In certain embodiments of the invention, the number of amino acid substitutions, insertions or deletions for any given CXCL13 polypeptide, fragment or variant will not be more than 1-5, or any range or value therein, as specified herein.

The CXCL13 polypeptides may also comprise modified, non-naturally occurring and unusual amino acids substituted or added to their amino acid sequences. A list of exemplary modified, non-naturally occurring and unusual amino acids is provided below.

| Modified (Unusual) Amino Acid | Symbol |
|---|---|
| 2-Aminoadipic acid | Aad |
| 3-Aminoadipic acid | Baad |
| beta-Alanine, beta-Aminopropionic acid | bAla |
| 2-Aminobutyric acid | Abu |
| 4-Aminobutyric acid, piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | Baib |
| 2-Aminopimelic acid | Apm |
| 2,4-Diaminobutyric acid | Dbu |
| Desmosine | Des |
| 2,2'-Diaminopimelic acid | Dpm |
| 2,3-Diaminopropionic acid | Dpr |
| N-Ethylglycine | EtGly |
| N-Ethylasparagine | EtAsn |
| Hydroxylysine | Hyl |
| Allo-Hydroxylysine | Ahyl |
| 3-Hydroxyproline | 3Hyp |
| 4-Hydroxyproline | 4Hyp |
| Isodesmosine | Ide |
| Allo-Isoleucine | Aile |
| N-Methylglycine, sarcosine | MeGly |
| N-Methylisoleucine | MeIle |
| 6-N-Methyllysine | MeLys |
| N-Methylvaline | MeVal |
| Norvaline | Nva |
| Norleucine | Nle |
| Ornithine | Orn |

Amino acids in a CXCL13 polypeptide that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one CXCL13 neutralizing activity.

Such variants have an altered amino acid sequence and can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade that includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a CXCL13 polypeptide that function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods that can be used to produce libraries of potential variants of the CXCL13 polypeptide from a degenerate oligonucleotide sequence. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the coding sequence of a CXCL13 polypeptide can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a CXCL13 Antagonist polypeptide (Arkin and Yourvan (1992) *Proc. Natl. Acad. Sci. USA* 89:7811-7815; Delgrave et al. (1993) *Protein Engineering* 6(3):327-331).

Compositions and their Uses

In accordance with the invention, the neutralizing CXCL13 antagonists, such as monoclonal antibodies, described herein can be used to inhibit CXCL13 activity. Additionally, such antagonists can be used to inhibit CXCL13-related inflammatory diseases amenable to such treatment, which may include, but are not limited to, pulmonary-related disorders. The individual to be treated may be any mammal and is preferably a primate, a companion animal which is a mammal and, most preferably, a human patient. The amount of antagonist administered will vary according to the purpose it is being used for and the method of administration.

The anti-CXCL13 antagonists may be administered by any number of methods that result in an effect in tissue in which CXCL13 activity is desired to be prevented or halted. Further, the CXCL13 antagonists need not be present locally to impart an effect on the CXCL13 activity; therefore, they may be administered wherever access to body compartments or fluids containing CXCL13 is achieved. In the case of inflamed, malignant, or otherwise compromised tissues, these methods may include direct application of a formulation containing the antagonists. Such methods include intravenous administration of a liquid composition, transdermal administration of a liquid or solid formulation, oral, topical administration, or interstitial or inter-operative administration. Adminstration may be affected by the implantation of a device whose primary function may not be as a drug delivery vehicle.

Administration may also be oral or by local injection into a tumor or tissue but generally, a monoclonal antibody is administered intravenously. Generally, the dosage range is from about 0.05 mg/kg to about 12.0 mg/kg. This may be as a bolus or as a slow or continuous infusion which may be controlled by a microprocessor controlled and programmable pump device.

Alternatively, DNA encoding preferably a fragment of a monoclonal antibody may be isolated from hybridoma cells and administered to a mammal. The DNA may be administered in naked form or inserted into a recombinant vector, e.g., vaccinia virus, in a manner which results in expression of the DNA in the cells of the patient and delivery of the antibody.

The monoclonal antibody used in the method of the present invention may be formulated by any of the established methods of formulating pharmaceutical compositions, e.g., as described in Remington's Pharmaceutical Sciences, 1985. For ease of administration, the monoclonal antibody will typically be combined with a pharmaceutically acceptable carrier. Such carriers include water, physiological saline, or oils.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Except insofar as any conventional medium is incompatible with the active ingredient and its intended use, its use in any compositions is contemplated.

The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use.

The CXCL13 antagonist nucleic acid molecules, polypeptides, and antibodies can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In another aspect, the invention relates to CXCL13 antagonists, as described herein, which are modified by the covalent attachment of a moiety. Such modification can produce a CXCL13 antagonist with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms. As used herein, the term "fatty acid" encompasses mono-carboxylic acids and di-carboxylic acids. Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-delta 9-octadecanoate ($C_{18}$, oleate), all cis-delta5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human polypeptides and antibodies can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)).

The invention includes methods for preparing pharmaceutical compositions for modulating the expression or activity of a CXCL13 polypeptide, nucleic acid, or antibody. Such methods comprise formulating a pharmaceutically acceptable carrier with an agent that modulates expression or activity of a CXCL13 polypeptide, nucleic acid, or antibody. Such compositions can further include additional active agents. Thus, the invention further includes methods for preparing a pharmaceutical composition by formulating a pharmaceutically acceptable carrier with an agent that modulates expression or activity of a CXCL13 polypeptide, nucleic acid, or antibody and one or more additional active compounds.

The agent that modulates expression or activity can, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents and protein or polypeptide agents depend upon a number of factors within the knowledge of the ordinarily skilled physician, veterinarian, or researcher. The dose(s) of these agents will vary, for example, depending upon the identity, size, and condition of the subject or sample being treated, further depending upon the route by which the composition is to be administered, if applicable, and the effect which the practitioner desires the agent to have upon the CXCL13 polypeptide, nucleic acid, or antibody. Exemplary doses of a small molecule include milligram or microgram amounts per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). Exemplary doses of a protein or polypeptide include gram, milligram or microgram amounts per kilogram of subject or sample weight (e.g., about 1 microgram per kilogram to about 5 grams per kilogram, about 100 micrograms per kilogram to about 500 milligrams per kilogram, or about 1 milligram per kilogram to about 50 milligrams per kilogram). It is furthermore understood that appropriate doses of one of these agents depend upon the potency of the agent with respect to the expression or activity to be modulated. Such appropriate doses can be determined using the assays described herein.

When one or more of these agents is to be administered to an animal (e.g., a human) in order to modulate expression or activity of a CXCL13 polypeptide, nucleic acid, or antibody, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation or buccal), transdermal (topical), transmucosal, and rectal administration. Solutions or suspensions used for parenteral, intradermal, or subcutaneous application can include the following components: a sterile diluen, such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediamine-tetraacetic acid; buffers, such as acetates, citrates or phosphates and agents for the adjustment of tonicity, such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating, such as lecithin, by the maintenance of the required particle size in the case of dispersion and by the use of surfactants. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin. Pharmaceutical excipients and additives useful in stabilizing the present composition include, but are not limited to, polypeptides, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary but non-limiting polypeptide excipients include serum albumin, such as human serum albumin (HSA), recombinant human albumin (rHA), gelatin, casein, and the like. Representative amino acids, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium, and then incorporating the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. Non-limiting examples of, and methods of preparing such sterile solutions are well known in the art, such as, but limited to, Gennaro, Ed., *Remington's Pharmaceutical Sciences*, 18$^{th}$ Edition, Mack Publishing Co. (Easton, Pa.) 1990.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches, and the like can contain any of the following ingredients, or compounds of a similar nature: a binder, such as microcrystalline cellulose, gum tragacanth or gelatin; an excipient, such as starch or lactose, a disintegrating agent, such as alginic acid, Primogel, or corn starch; a lubricant, such as magnesium stearate or Sterotes; a glidant, such as colloidal silicon dioxide; a sweetening agent, such as sucrose or saccharin; or a flavoring agent, such as peppermint, methyl salicylate, or orange flavoring.

For administration by inhalation, the compounds are delivered in the form of aerosolized particles from a pressurized container or dispenser that contains a suitable propellant, e.g., a gas such as carbon dioxide, or a nebulizer. Alternatively, compositions formulated as particles can be dispersed by electrostatic, mechanical means including vibrations, or ultrasonic means as taught in U.S. Pat. Nos. 4,530,464; 4,533,082; 5,838,350; 6,113,001; 6,514,496; 5,518,179; 5,152,456; 5,261,601; and 4,605,167.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams, as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes having monoclonal antibodies incorporated therein or thereon) can also be used as pharmaceutically acceptable carriers. Particularly preferred compositions and methods are taught in U.S. Pat. Nos. 5,891,468 and 6,316,024.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is about 0.1 mg/kg to 100 mg/kg of body weight (generally about 10 mg/kg to 20 mg/kg). If the antibody is to act in the brain, a dosage of about 50 mg/kg to 100 mg/kg is usually appropriate. Generally, partially human antibodies and fully human antibodies have a longer half-life within the human body than other antibodies. Accordingly, the use of lower dosages and less frequent administration is often possible. Modifications, such as lipidation, can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The CXCL13 Antagonist nucleic acid molecules can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Pharmacogenomics

Agents, or modulators that have a stimulatory or inhibitory effect on activity or expression of a CXCL13 polypeptide as identified by a screening assay described herein, can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a CXCL13 polypeptide, expression of a CXCL13 nucleic acid, or mutation content of a CXCL13 gene in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism." These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a CXCL13 polypeptide, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

Methods of Treatment

The present invention provides for both prophylactic and therapeutic methods of treating a subject at risk of (or susceptible to) a disorder or having a disorder associated with aberrant expression or activity of a CXCL13 polypeptide and/or in which the CXCL13 polypeptide is involved.

The present invention provides a method for modulating or treating at least one CXCL13 related disease or condition, in a cell, tissue, organ, animal, or patient, as known in the art or as described herein, using at least one CXCL13 antagonist.

Compositions of CXCL13 antagonists may find therapeutic use in the treatment of pulmonary disorder-related conditions, such as asthma, emphysema, COPD, and neonatal chronic lung disease.

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, urticaria, systemic anaphalaxis, dermatitis, pernicious anemia, hemolytic disease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), acute promyelocytic leukemia (APL), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain, and the like.

Disorders characterized by aberrant expression or activity of the CXCL13 polypeptides are further described elsewhere in this disclosure.

1. Prophylactic Methods

In one aspect, the invention provides a method for at least substantially preventing in a subject, a disease or condition associated with an aberrant expression or activity of a CXCL13 polypeptide, by administering to the subject an agent that modulates expression or at least one activity of the polypeptide. Subjects at risk for a disease that is caused or contributed to by aberrant expression or activity of a CXCL13 polypeptide can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. The appropriate agent can be determined based on screening assays described herein.

2. Therapeutic Methods

Another aspect of the invention pertains to methods of modulating expression or activity of a CXCL13 polypeptide for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. In another embodiment, the agent inhibits one or more of the biological activities of the CXCL13 polypeptide. Examples of such inhibitory agents include antisense nucleic acid molecules and antibodies and other methods described herein. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a CXCL13 polypeptide. In one embodiment, the method involves administering an agent (e.g., an agent identified by a screening assay described herein), or combination of agents that modulate (e.g., up-regulates or down-regulates) expression or activity. Inhibition of activity is desirable in situations in which activity or expression is abnormally high or up-regulated and/or in which decreased activity is likely to have a beneficial effect.

A method of the present invention comprises administering an effective amount of a composition or pharmaceutical composition comprising at least one CXCL13 antagonist or specified portion or variant to a cell, tissue, organ, animal or patient in need of such modulation, treatment or therapy. Such a method can optionally further comprise co-administration or combination therapy for treating such immune diseases, wherein the administering of said at least one CXCL13 antagonist, specified portion or variant thereof, further comprises administering, before concurrently, and/or after, at least one selected from at least one of glutiramer acetate (e.g., Copaxone), cyclophasphamide, azathioprine, glucocorticosteroids, methotrexate, Paclitaxel, 2-chlorodeoxyadenosine, mitoxantrone, IL-10, TGBb, CD4, CD52, antegren, CD11, CD18, TNFalpha, IL-1, IL-2, and/or CD4 antibody or antibody receptor fusion, interferon alpha, immunoglobulin, Lismide (Requinimax™), insulin-like growth factor-1 (IGF-1), elprodil, pirfenidone, oral myelin, or compounds that act on one or more of at least one of: autoimmune suppression of myelin destruction, immune regulation, activation, proliferation, migration and/or suppressor cell function of T-cells, inhibition of T cell receptor/peptide/MHC-II interaction, Induction of T cell anergy, deletion of autoreactive T cells, reduction of trafficking across blood brain barrier, alteration of balance of pro-inflammatory (Th1) and immunomodulatory (Th2) cytokines, inhibition of matrix metalloprotease inhibitors, neuroprotection, reduction of gliosis, promotion of re-myelination), TNF antagonist (e.g., but not limited to, a TNF Ig derived protein or fragment, a soluble TNF receptor or fragment, fusion proteins thereof, or a small molecule TNF antagonist), an antirheumatic, a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, an antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

TNF antagonists suitable for compositions, combination therapy, co-administration, devices and/or methods of the present invention (further comprising at least one antibody, specified portion and variant thereof, of the present invention), include, but are not limited to, anti-TNF Ig derived proteins, antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor Ig derived protein," "TNF Ig derived protein," "TNFα Ig derived protein," or fragment and the like decreases, blocks, inhibits, abrogates or interferes with TNFα activity in vitro, in situ and/or preferably in vivo. For example, a suitable TNF human Ig derived protein of the present invention can bind TNFα and includes anti-TNF Ig derived proteins, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

Chimeric Ig derived protein cA2 consists of the antigen binding variable region of the high-affinity neutralizing mouse anti-human TNFα IgG1 Ig derived protein, designated A2, and the constant regions of a human IgG1, kappa immunoglobulin. The human IgG1 Fc region improves allogeneic Ig derived protein effector function, increases the circulating serum half-life and decreases the immunogenicity of the Ig derived protein. The avidity and epitope specificity of the chimeric Ig derived protein cA2 is derived from the variable region of the murine Ig derived protein A2. In a particular embodiment, a preferred source for nucleic acids encoding the variable region of the murine Ig derived protein A2 is the A2 hybridoma cell line.

Chimeric A2 (cA2) neutralizes the cytotoxic effect of both natural and recombinant human TNFα in a dose dependent manner. From binding assays of chimeric Ig derived protein cA2 and recombinant human TNFα, the affinity constant of chimeric Ig derived protein cA2 was calculated to be $1.04 \times 10^{10} M^{-1}$. Preferred methods for determining monoclonal Ig derived protein specificity and affinity by competitive inhibition can be found in Harlow, et al., *Ig derived proteins: A Laboratory Manual*, Cold Spring Harbor Laboratory Press, Cold Spring Harbor, N.Y., 1988; Colligan et al., eds., *Current Protocols in Immunology*, Greene Publishing Assoc. and Wiley Interscience, New York, (1992-2003); Kozbor et al., *Immunol. Today*, 4:72-79 (1983); Ausubel et al., eds. *Current Protocols in Molecular Biology*, Wiley Interscience, New York (1987-2003); and Muller, *Meth. Enzymol.*, 92:589-601 (1983), which references are entirely incorporated herein by reference.

In a particular embodiment, murine monoclonal Ig derived protein A2 is produced by a cell line designated c134A. Chimeric Ig derived protein cA2 is produced by a cell line designated c168A.

Additional examples of monoclonal anti-TNF Ig derived proteins that can be used in the present invention are described in the art (see, e.g., U.S. Pat. No. 5,231,024; Möller, A. et al., *Cytokine* 2(3):162-169 (1990); U.S. application Ser. No. 07/943,852 (filed Sep. 11, 1992); Rathjen et al., International Publication No. WO 91/02078 (published Feb. 21, 1991); Rubin et al., EPO Patent Publication No. 0 218 868 (published Apr. 22, 1987); Yone et al., EPO Patent Publication No. 0 288 088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); and Hirai, et al., *J. Immunol. Meth.* 96:57-62 (1987), which references are entirely incorporated herein by reference).

TNF Receptor Molecules

Preferred TNF receptor molecules useful in the present invention are those that bind TNFα with high affinity (see, e.g., Feldmann et al., International Publication No. WO 92/07076 (published Apr. 30, 1992); Schall et al., *Cell* 61:361-370 (1990); and Loetscher et al., *Cell* 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J. Biochem.* 223:831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., *J. Biol. Chem.* 265:1531-1536 (1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high affinity, as well as other undefined properties, may contribute to the therapeutic results achieved.

TNF receptor multimeric molecules useful in the present invention comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule. These multimeric molecules and methods for their production have been described in U.S. application Ser. No. 08/437,533 (filed May 9, 1995), the contents of which are entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al., *Cytokine* 6(6):616-623 (1994); Baker et al., *Eur. J. Immunol.* 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116,964; Capon et al., U.S. Pat. No. 5,225,538; and Capon et al., *Nature* 337:525-531 (1989), which references are entirely incorporated herein by reference.

A functional equivalent, derivative, fragment or region of TNF receptor molecule refers to the portion of the TNF receptor molecule, or the portion of the TNF receptor molecule sequence which encodes TNF receptor molecule, that is of sufficient size and sequences to functionally resemble TNF receptor molecules that can be used in the present invention (e.g., bind TNFα with high affinity and possess low immunogenicity). A functional equivalent of TNF receptor molecule also includes modified TNF receptor molecules that functionally resemble TNF receptor molecules that can be used in the present invention (e.g., bind TNFα with high affinity and possess low immunogenicity). For example, a functional equivalent of TNF receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid).

See Ausubel et al., *Current Protocols in Molecular Biology*, Greene Publishing Assoc. and Wiley-Interscience, New York (1987-2003).

While having described the invention in general terms, the embodiments of the invention will be further disclosed in the following examples which should not be construed as limiting the scope of the claims.

EXAMPLE 1

CXCL13 mRNA Transcript Levels are Elevated in Diseased Lung Tissues

The levels of mRNA transcripts encoding the CXCL13 protein are elevated in the lung tissue of untreated SP-C/TNFα mice, and SP-C/TNFα mice treated with a TNFα specific mAb relative to control C57BL6 mice (FIG. 1). SP-C/TNF-alpha mice are transgenic mice derived from the C57BL6 mouse strain that constituatively over-express murine TNFα in the lung tissues Over expression of TNFα in the lung (SP-C/TNFα transgenic mice) causes many pathological changes similar to those found in COPD patients, including pulmonary inflammation, emphysema, pulmonary fibrosis [16] and the formation of ectopic lymphoid follicles. SP-C/TNFα mice are a model for such pulmonary diseases as pulmonary inflammation emphysema, pulmonary fibrosis, and Congestive Obstructive Pulmonary Disease (COPD). The formation of ectopic lymphoid follicles in the lungs is a pathology associated with each of these pulmonary diseases. Ectopic lyphoid follicles in the lungs can be formed through B cell infiltration into lung and other pulmonary tissues. The results in FIG. 1 indicate that increased CXCL13 protein levels in the lung tissues of SP-C/TNFα mice contribute to the formation of ectopic lymphoid follicles in the lungs and the onset of associated pulmonary diseases in these animals.

For this experiment, twelve-week old control C57BL6 mice and untreated SP-C/TNFα mice received intraperitoneal injections of 200 µL of PBS every Monday and Friday for six weeks. SP-C/TNFα mice received 0.5 mg of the TNFα specific cV1q mAb in 200 µL of PBS by intraperitoneal injection every Monday and Friday for six weeks. The cV1q mAb is a monoclonal rat IgG1 isotype monoclonal antibody that binds murine TNFα. The cV1q mAb was generated using standard methods. Six weeks after injections started, mice were sacrificed in compliance with institutional animal care and use guidelines.

Lungs were removed from sacrificed animals, homogenized, and mRNA was extracted and isolated using standard methods. RT-PCR specific for CXCL13 mRNAs and GAPDH mRNAs was also performed using standard methods. CXCL13 and GAPDH mRNA levels were then quantified using standard methods and CXCL13 mRNA levels were normalized to GAPDH housekeeping gene mRNA levels. Data presented represent the mean+/−the standard deviation of the normalized CXCL13 mRNA levels from 5 different mice (FIG. 1).

EXAMPLE 2

Figure 2:
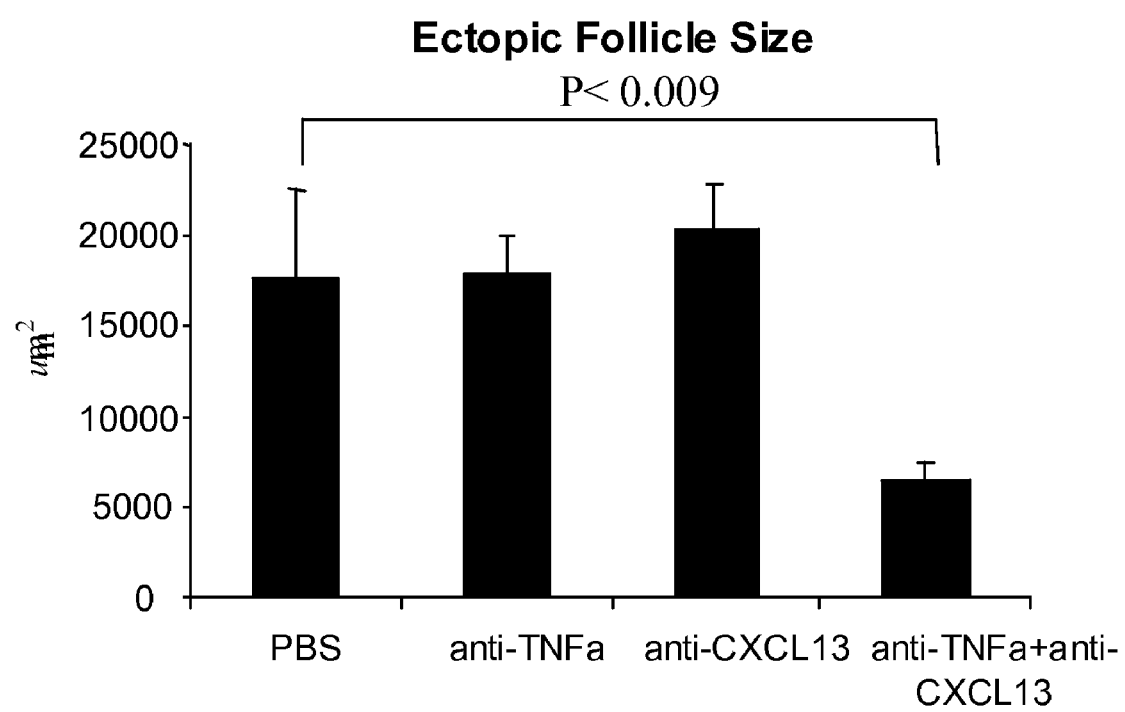
FIG. 2 shows that co-treatment with monoclonal antibodies specific for TNF-α and CXCL13 alleviate lung disease symptoms as assessed by ectopic follicle size in diseased lung tissues.
Figure 3:
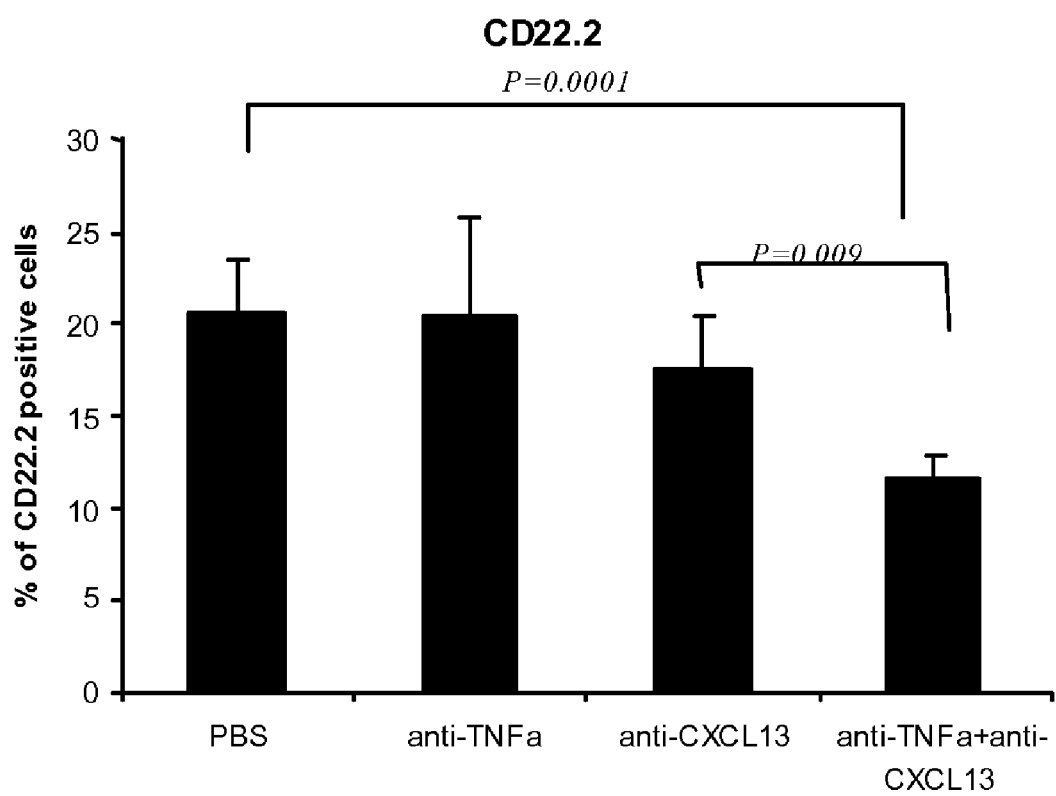
FIG. 3 shows that co-treatment with monoclonal antibodies specific for TNF-α and CXCL13 decrease infiltration of B-cells expressing CD22.2 into lung tissues.
Figure 4:
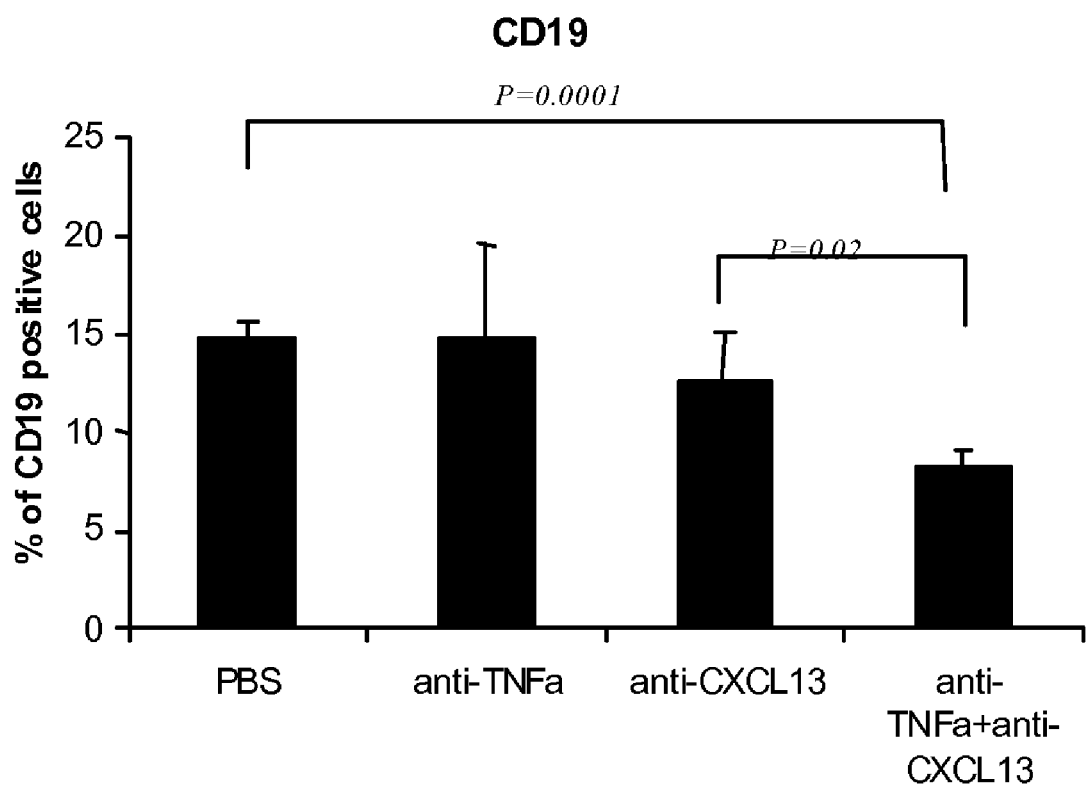
FIG. 4 shows that co-treatment with monoclonal antibodies specific for TNF-α and CXCL13 decrease infiltration of B-cells expressing CD19 into lung tissues.
Figure 5:
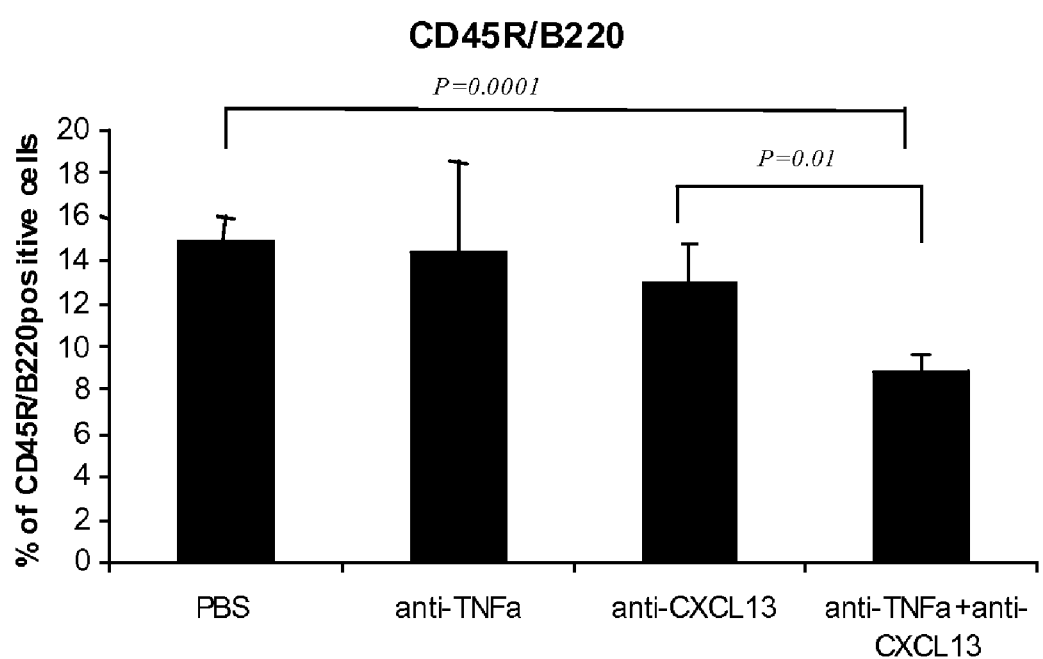
FIG. 5 shows that co-treatment with monoclonal antibodies specific for TNF-α and CXCL13 decrease infiltration of B-cells expressing CD45R/B220 into lung tissues.
Figure 6:
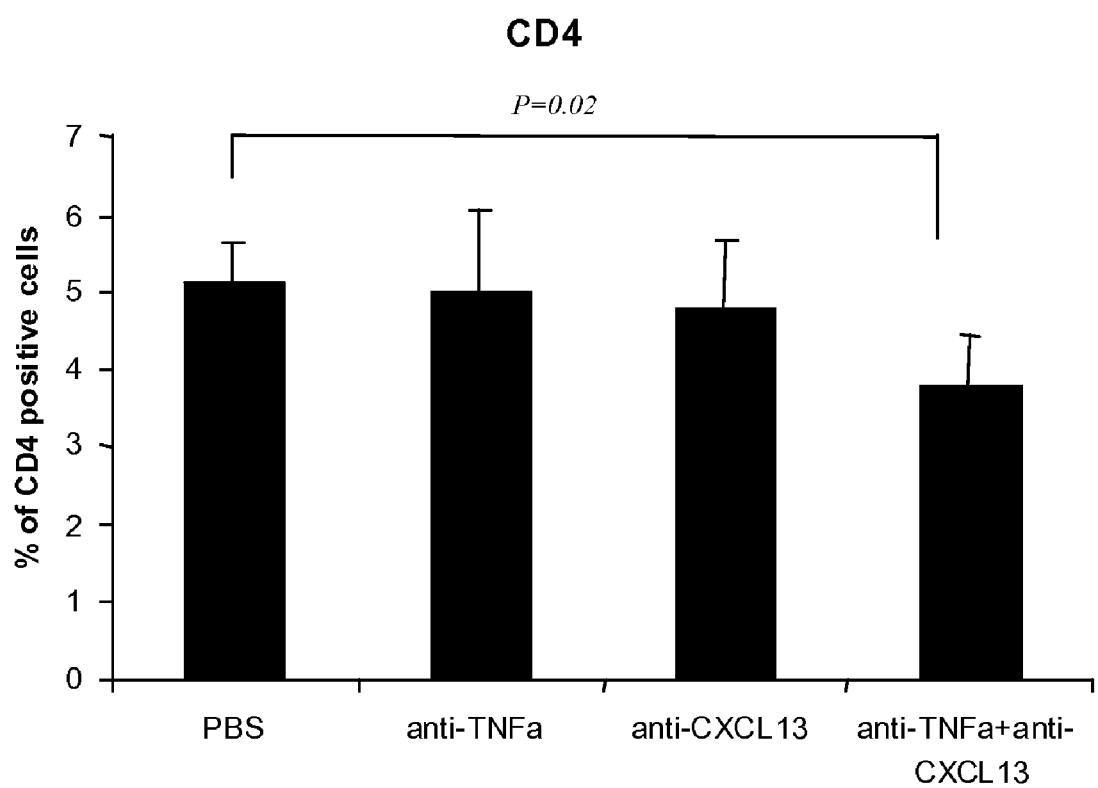
FIG. 6 shows that co-treatment with monoclonal antibodies specific for TNF-α and CXCL13 decrease infiltration of B-cells expressing CD4 into lung tissues.

Co-Treatment with Monoclonal Antibodies Specific for TNFα and CXCL13 Alleviate Lung Disease Symptoms Co-administration of mAbs specific for TNFα and CXCL13 alleviate lung disease associated symptoms in SP-C/TNFα mice (FIG. 2). Ectopic follicle size was significantly reduced in SP-C/TNFα mice co-treated with mAbs specific for TNFα and CXCL13 relative to untreated control animals (FIG. 2). In SP-C/TNFα transgenic mice treated with anti-TNFα mAb for 8 weeks, airway infiltration of neutrophils was significantly reduced; however, treatment had little impact on the ectopic lymphoid follicles. This finding indicates that once formed, the ectopic lymphoid follicles maintain their homeostasis in a TNFα independent fashion.

For this experiment, twelve-week old control SP-C/TNFα mice received intraperitoneal injections every Monday and Friday for six weeks. Control animals received injections of 200 µL of PBS alone. Anti-TNFα treated animals received 0.5 mg of the TNFα specific cV1q mAb in 200 µL of PBS. Anti-CXCL13 treated animals received 0.5 mg of the CXCL13 specific MAB4701 mAb in 200 µL of PBS. Co-treated animals received 0.5 mg of the TNFα specific cV1q mAb and 0.5 mg of the CXCL13 specific MAB4701 mAb in 200 µL of PBS. MAB4701 is a monoclonal rat IgG1 isotype monoclonal antibody that binds murine CXCL13. The MAB4701 mAb was generated using standard methods and is available commercially (R&D Systems, Inc., Minneapolis, Minn.). Six weeks after injections started, mice were sacrificed in compliance with institutional animal care and use guidelines. Lungs were removed from sacrificed animals, sectioned, slides prepared and histopathological analyses were performed to quantitate ectopic follicle size and formation using standard methods. A Phase 3 Imaging System (Glen Mills, Pa.) and associated analytical software was used to perform microscopy and measure the size of 10-20 follicles per tissue slide per mouse. Data presented (FIG. 2) represent the mean+/−the standard deviation of the results from analyses of 5 different mice from each treatment group.

It is hypothesized that the results described above may indicate that anti-CXCL13 therapy alone may be useful in treating respiratory-related diseases. Because the mouse model has increased expression of TNFα, inhibition of TNFα along with anti-CXCL13 therapy may be necessary to show amelioration of the disease state in this model. For models in which TNFα is not overexpressed, inhibition of CXCL13 may be sufficient for amelioration of the disease state. Additionally, in the model described above, TNF expression is through transgenic animals and is independent of disease progression. In a pathological situation, e.g., patient treatment, TNF expression most likely will be reduced with the reduction of inflammation, so if a CXCL13 antagonist can reduce the migration and accumulation of TNFα producing cells, it alone could be therapeutically effective. This is tested in in vivo disease models.

EXAMPLE 3

Co-Treatment with Monoclonal Antibodies Specific for TNF-Alpha and CXCL13 Decrease B-Cell Infiltration into Lung Tissues Co-administration of mAbs specific for TNFα and CXCL13 decrease B-cell infiltration into lung tissues (FIGS. 3, 4, 5, and 6). B-cell infiltration was assayed by flow cytometry via detection of the CD22.2, CD19, CD45R/B220, and CD4 B-cell markers, respectively. B-cell infiltration in lung tissue was significantly reduced in SP-C/TNFα mice co-treated with mAbs specific for TNFα and CXCL13 relative to untreated control animals (FIGS. 3, 4, 5, and 6).

Animals were prepared and treatments performed as described in Example 2 above. Six weeks after injections started, mice were sacrificed in compliance with institutional animal care and use guidelines. Lung tissues were then minced and digested with collagenase VII (1500 IU/ml) at 37° C. for 45 minutes to liberate individual cells. Cell preparations were then incubated with labeled, commercially available CD22.2 (FIG. 3), CD19 (FIG. 4), CD45R/B220 (FIG. 5), and CD4 (FIG. 6) specific mAbs using standard methods. B-cells in the cell population prepared carry either the CD22.2, CD19, CD45R/B220, or CD4 markers and are detectably labeled after incubation with the commercially available CD22.2, CD19, CD45R/B220, or CD4 mAbs. This labeling is the basis for the identification of B-cells by flow cytometry. Flow cytometry analysis was performed on cell populations using standard methods and the percentage of B-cells present in the cell population was then determined, for each marker, using standard methods. Data presented (FIGS. 3, 4, 5, and 6) represent the mean+/−the standard deviation of the results from analyses of the lung cell preparations of 5 different mice from each treatment group.

The sequences of CXCL13, CXCR5, and TNFα described herein are as follows:

TABLE 3

| SEQ ID NO | Nucleotide/Protein | Name/Species |
|---|---|---|
| 1 | Nucleotide | Murine CXCL13 |
| 2 | Protein | Murine CXCL13 |
| 3 | Nucleotide | Human CXCL13 |
| 4 | Protein | Human CXCL13 |
| 5 | Nucleotide | Murine TNFα |
| 6 | Protein | Murine TNFα |
| 7 | Nucleotide | Human TNFα |
| 8 | Protein | Human TNFα |
| 9 | Nucleotide | Human CXCR-5 |
| 10 | Protein | Human CXCR-5 |
| 11 | Nucleotide | Murine CXCR-5 |
| 12 | Protein | Murine CXCR-5 |

EXAMPLE 4

Co-Administration of Monoclonal Antibodies Specific for TNFα and CXCL13 Treats Kidney Pathologies Associated with Systemic Lupus Erythematosus Co-administration of mAbs specific for CXCL-13 and TNFα treated kidney pathologies associated with systemic lupus erythematosus (SLE) in a murine model of SLE. Glomerulonephritis is an inflammation of internal kidney structures called glomeruli and is a hallmark of SLE. Proteinuria is the excessive secretion of serum proteins into the urine and is a measure of kidney disease resulting from SLE associated glomerlonephritis. Histological changes in the kidney tissues, such as the formation of periarterial lymphocytic infiltrate foci, are another hallmark of kidney disease resulting from SLE associated glomerlonephritis.

Figure 7:
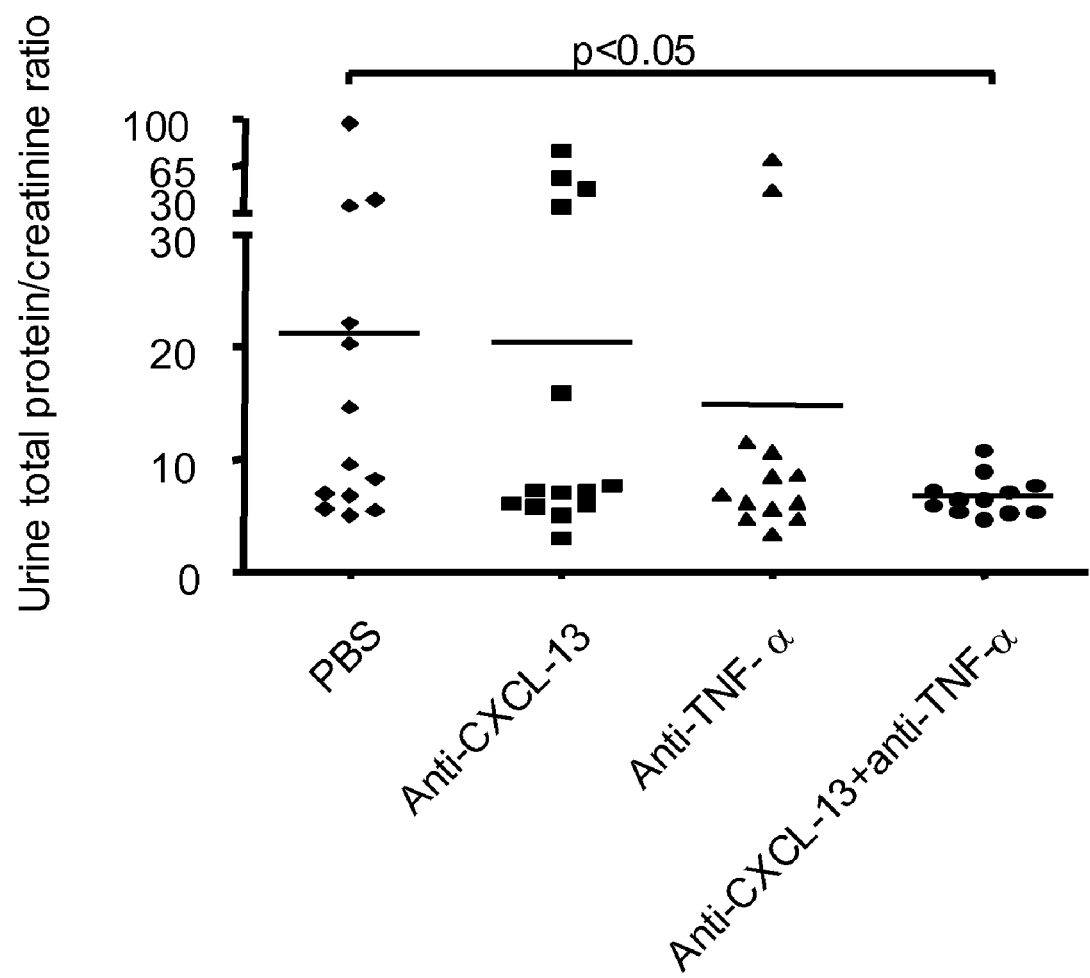
FIG. 7 shows that co-administration of mAbs specific for CXCL-13 and TNF-α decreased glomerlonephritis associated protein levels in the urine of NZB/W F1 mice exhibiting systemic lupus erythematosus (SLE) symptoms to levels below that of untreated control NZB/W F1 mice that received PBS vehicle alone.

Co-administration of mAbs specific for CXCL-13 and TNFα decreased glomerlonephritis associated protein levels in the urine of NZB/W F1 mice exhibiting SLE symptoms to levels below that of untreated control NZB/W F1 mice that received PBS vehicle alone (FIG. 7).

Figure 8:
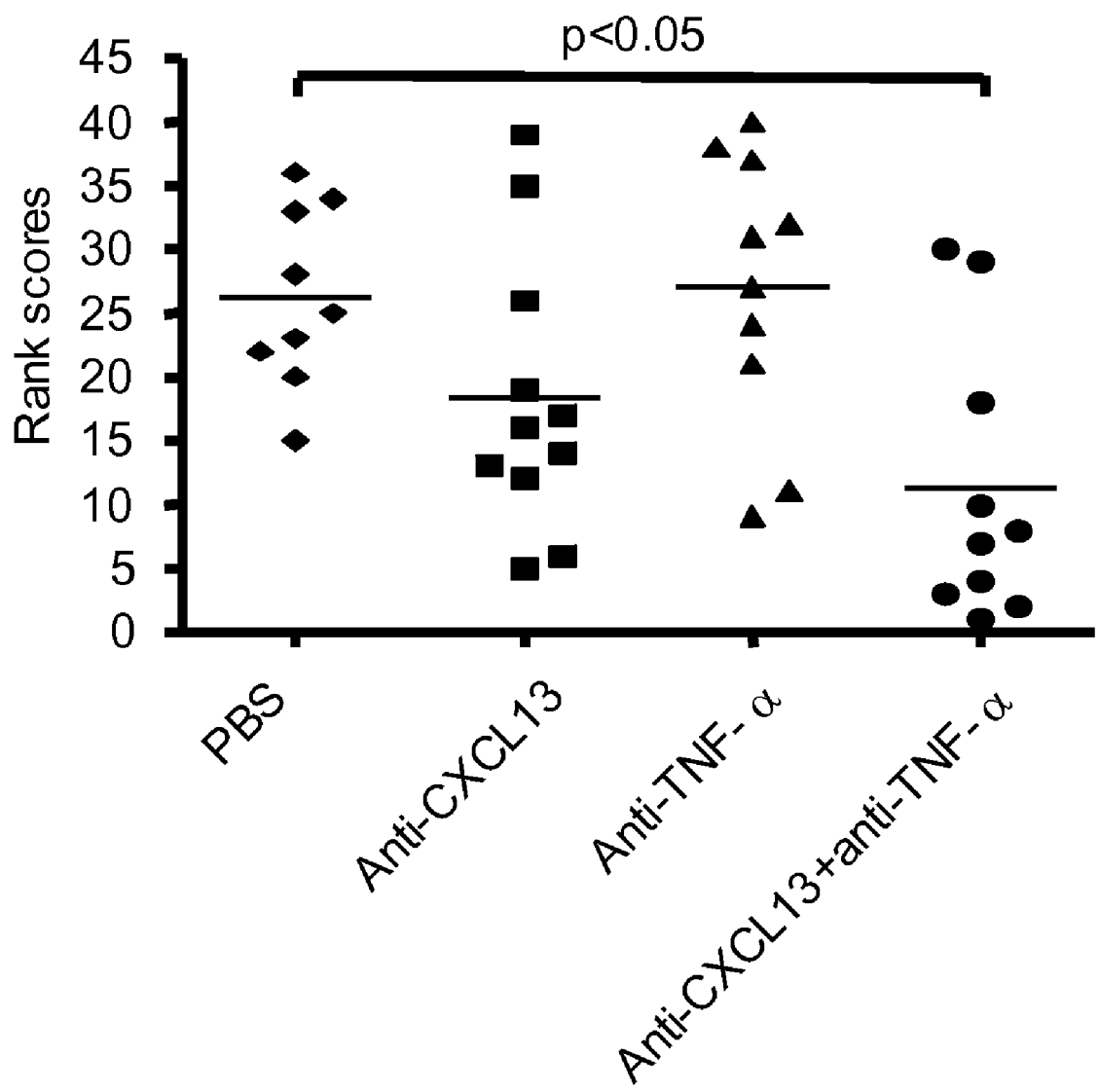
FIG. 8 shows that co-administration of mAbs specific for CXCL-13 and TNF-α decreased the rank scored severity of systemic lupus erythematosus (SLE) associated kidney disease in NZB/W F1 mice exhibiting SLE symptoms to levels below that of untreated control NZB/WF1 mice that received PBS vehicle alone (FIG. 8).

Additionally, co-administration of mAbs specific for CXCL-13 and TNFα decreased the rank scored severity of SLE associated kidney disease in NZB/W F1 mice exhibiting SLE symptoms to levels below that of untreated control NZB/WF1 mice that received PBS vehicle alone (FIG. 8). The severity of SLE associated kidney disease in NZB/W F1 mice was determined using a ranked scoring system. Scores were based on the number of periarterial lymphocyte infiltrate foci identified by histological examination of the kidney tissues and the severity of glomerlonephritis associated protein levels in the kidney tissues of NZB/W F1 mice from each treatment group (FIG. 8).

For these experiments, 12-week old NZB/W F1 mice were obtained from Jackson Labs (Bar Harbor, Me.). NZB/W F1 mice present systemic lupus erythematosus (SLE)-like symptoms as they age and are an accepted murine model of SLE. On day 0, the study animals were randomly assigned to control or treatment groups (n=15/group). Animals were administered an intraperitoneal injection of PBS vehicle (control animals), anti-CXCL13 mAb (1 mg per mouse in PBS), anti-TNFα mAb (1 mg per mouse in PBS), or both the anti-CXCL13 mAb (1 mg per mouse in PBS) and the anti-TNFα mAb (1 mg per mouse in PBS) weekly from 18 weeks of age through 38 weeks of age. The anti-CXCL13 mAb is a neutralizing rat anti-CXCL13 mAb (R&D Systems Inc., Minneapolis, Minn.). The anti-TNF-alpha mAb is a chimarized rat anti-TNF-alpha mAb from Centocor, Inc. which was generated using standard methods. Animals were monitored weekly. Urine was collected periodically via free catch and stored at −80° C. Animals were sacrificed at the end of the study and kidneys were harvested into appropriate storage buffers before further analysis. Animals were cared for, handled, and sacrificed using approved institutional animal care and use guidelines.

The total protein and creatine present in the urine collected was determined using standard methods and an Ace Analyzer (Alpha Wasserman, West Caldwell, N.J.). Urine total protein was measured in 100 µl of undiluted urine samples, and creatinine was measured in 100 µl of 1:10 diluted urine samples in deionized distilled $H_2O$. These values were then used to calculate the resulting ratio of urine total protein to creatine. Urine total protein/creatinine ratio were expressed as mean plus or minus standard error and statistically significant differences between samples was determined using a two tailed analysis of variance by standard t-test at a p-value<0.05.

Histological analysis was performed on kidneys harvested when animals were 38 weeks old. Harvested kidney's were immediately immersed in a 0.7% periodate lysine paraformaldehyde (PLP) buffer composed of 0.1 M phosphate buffer, 0.7% paraformaldehyde, 75 mM L lysine, and 10 mM $NaIO_4$. The kidneys were embedded in paraffin blocks after overnight fixation with the PLP buffer. Standard methods were used for the preparation of 7 µM sections and hematoxylin and eosin staining. Samples were examined and scored for SLE associated kidney disease severity in a blinded fashion. Scoring was based on the number of periarterial lymphocyte infiltrate foci identified by histological examination of the kidney tissues and the severity of glomerlonephritis associated protein levels in the kidney tissues of NZB/W F1 mice from each treatment group. Kruskal-Wallis Analysis of Variance on Ranks analysis was performed with Dunn's correction for multiple comparisons and a p-value<0.05 was used to identify differences between treatment groups to be accepted as statistically significant.

Although illustrated and described above with reference to certain specific embodiments, the present invention is nevertheless not intended to be limited to the details shown. Rather, the present invention is directed to the CXCL13 antagonist polypeptides, polynucleotides, antibodies, apparatus, and kits disclosed herein and uses thereof, and methods for controlling the levels of CXCL13, optionally along with controlling the levels of TNF-α, and various modifications may be made in the details within the scope and range of equivalents of the claims and without departing from the spirit of the invention.

---

We claim:

1. A method for treating a CXCL13 activity-related disorder in a cell, tissue, organ or animal comprising:
   administering to the cell, tissue, organ or animal a CXCL13 binding monoclonal antibody or a CXCL13 binding fragment thereof in an amount effective to inhibit the CXCL13 activity in said cell, tissue, organ or animal; and
   administering to the cell, tissue, organ or animal a TNFα binding monoclonal antibody or a TNFα binding fragment thereof in an amount effective to inhibit TNFα activity in said cell, tissue, organ or animal, wherein the CXCL13 activity-related disorder is chronic obstructive pulmonary disorder (COPD) or systemic lupus erythematosus.

2. The method of claim 1, wherein the antibody fragment is a Fab, Fab', or F(ab')2 fragment.

3. The method of claim 1, wherein the animal is a mammal.

4. The method of claim 3, wherein at least one monoclonal antibody or fragment is administered by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, and transdermal.

5. The method of claim 4, wherein a monoclonal antibody or fragment is administered in the amount of from about 0.05 mg/kg to about 30.0 mg/kg body weight of said mammal.

6. The method of claim 4, wherein the mammal is a human patient.

7. The method of claim 4, wherein a monoclonal antibody or fragment is administered intraperitoneally.

8. The method of claim 5, wherein a monoclonal antibody or fragment is administered in a bolus dose followed by an infusion of said antibody.

9. A method for treating an animal with systemic lupus erythematosus comprising:
   a) providing a of CXCL-13 binding antibody or CXCL-13 binding fragment of an antibody to the animal, and
   b) providing a of TNFα binding antibody or a TNFα binding fragment of an antibody to the animal;
   wherein each antibody or binding fragment is provided in an amount effective to cause a decrease in a symptom of systemic lupus erythematosus in the animal.

10. The method of claim 9, wherein the animal is a mammal.

11. The method of claim 10, wherein the mammal is a human.

12. The method of claim 9, wherein the amount of each antibody or binding fragment of an antibody provided is from about 0.05 mg per kg to about 50.0 mg per kg body weight of the animal.

13. The method of claim 12, wherein the amount of each antibody or binding fragment of an antibody provided is from about 25 mg per kg body weight of the animal to about 40 mg per kg body weight of the animal.

14. The method of claim 9, wherein the symptom of systemic lupus erythematosus is the number of periarterial lymphocyte infiltrate foci identified by examination of the kidney tissues.

15. The method of claim 9, wherein the symptom of systemic lupus erythematosus is the ratio of total urine protein to total urine creatinine.

* * * * *

SEQUENCE LISTING

<160> NUMBER OF SEQ ID NOS: 12

<210> SEQ ID NO 1
<211> LENGTH: 327
<212> TYPE: DNA
<213> ORGANISM: Mus musculus

<400> SEQUENCE: 1

```
atgaggctca gcacagcaac gctgcttctc ctcctggcca gctgcctctc tccaggccac      60
ggtattctgg aagcccatta cacaaactta aaatgtaggt gttctggagt gatttcaact     120
gttgtcggtc taaacatcat agatcggatt caagttacgc ccctgggaa tggctgcccc      180 aaaactgaag ttgtgatctg gaccaagatg aagaaagtta tatgtgtgaa tcctcgtgcc     240
aaatggttac aaagattatt aagacatgtc caaagcaaaa gtctgtcttc aactccccaa     300
gctccagtga gtaagagaag agctgcc                                          327
```

<210> SEQ ID NO 2
<211> LENGTH: 109
<212> TYPE: PRT
<213> ORGANISM: Mus musculus

<400> SEQUENCE: 2

```
Met Arg Leu Ser Thr Ala Thr Leu Leu Leu Leu Ala Ser Cys Leu
 1               5                  10                  15

Ser Pro Gly His Gly Ile Leu Glu Ala His Tyr Thr Asn Leu Lys Cys
                20                  25                  30

Arg Cys Ser Gly Val Ile Ser Thr Val Val Gly Leu Asn Ile Ile Asp
            35                  40                  45

Arg Ile Gln Val Thr Pro Pro Gly Asn Gly Cys Pro Lys Thr Glu Val
        50                  55                  60

Val Ile Trp Thr Lys Met Lys Lys Val Ile Cys Val Asn Pro Arg Ala
65                  70                  75                  80

Lys Trp Leu Gln Arg Leu Leu Arg His Val Gln Ser Lys Ser Leu Ser
                85                  90                  95

Ser Thr Pro Gln Ala Pro Val Ser Lys Arg Arg Ala Ala
            100                 105
```

<210> SEQ ID NO 3
<211> LENGTH: 327
<212> TYPE: DNA
<213> ORGANISM: Homo sapiens

<400> SEQUENCE: 3

```
atgaagttca tctcgacatc tctgcttctc atgctgctgg tcagcagcct ctctccagtc      60
caaggtgttc tggaggtcta ttacacaagc ttgaggtgta gatgtgtcca agagagctca     120
gtctttatcc ctagacgctt cattgatcga attcaaatct gccccgtgg gaatggttgt      180 ccaagaaaag aaatcatagt ctggaagaag aacaagtcaa ttgtgtgtgt ggaccctcaa     240
gctgaatgga tacaaagaat gatggaagta ttgagaaaaa gaagttcttc aactctacca     300
gttccagtgt ttaagagaaa gattccc                                          327
```

<210> SEQ ID NO 4
<211> LENGTH: 109
<212> TYPE: PRT
<213> ORGANISM: Homo sapiens

<400> SEQUENCE: 4

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
            20                  25                  30

Cys Arg Cys Val Gln Glu Ser Ser Val Phe Ile Pro Arg Arg Phe Ile
        35                  40                  45

Asp Arg Ile Gln Ile Leu Pro Arg Gly Asn Gly Cys Pro Arg Lys Glu
    50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
            100                 105

<210> SEQ ID NO 5
<211> LENGTH: 705
<212> TYPE: DNA
<213> ORGANISM: Mus musculus

<400> SEQUENCE: 5
atgagcacag aaagcatgat ccgcgacgtg aactggcag aagaggcact cccccaaaag    60 atgggggct tccagaactc caggcggtgc ctatgtctca gcctcttctc attcctgctt   120
gtggcagggg ccaccacgct cttctgtcta ctgaacttcg gggtgatcgg tccccaaagg   180
gatgagaagt tcccaaatgg cctccctctc atcagttcta tggcccagac cctcacactc   240
agatcatctt ctcaaaattc gagtgacaag cctgtagccc acgtcgtagc aaaccaccaa   300
gtggaggagc agctggagtg gctgagccag gcgccaacg ccctcctggc caacggcatg    360
gatctcaaag acaaccaact agtggtgcca gccgatgggt tgtaccttgt ctactcccag   420
gttctcttca agggacaagg ctgccccgac tacgtgctcc tcacccacac cgtcagccga   480
tttgctatct cataccagga gaaagtcaac ctcctctctg ccgtcaagag cccctgcccc   540
aaggacaccc ctgagggggc tgagctcaaa ccctggtatg agcccatata cctgggagga   600
gtcttccagc tggagaaggg ggaccaactc agcgctgagg tcaatctgcc caagtactta   660
gactttgcgg agtccgggca ggtctacttt ggagtcattg ctctg                   705

<210> SEQ ID NO 6
<211> LENGTH: 234
<212> TYPE: PRT
<213> ORGANISM: Mus musculus

<400> SEQUENCE: 6

Met Ser Thr Glu Ser Met Ile Arg Asp Val Glu Leu Ala Glu Glu Ala
1               5                   10                  15

Leu Pro Gln Lys Met Gly Gly Phe Gln Asn Ser Arg Arg Cys Leu Cys
            20                  25                  30

Leu Ser Leu Phe Ser Phe Leu Leu Val Ala Gly Ala Thr Thr Leu Phe
        35                  40                  45

Cys Leu Leu Asn Phe Gly Ile Gly Pro Gln Arg Asp Glu Lys Phe Pro
    50                  55                  60

```
Asn Gly Leu Pro Leu Ile Ser Ser Met Ala Gln Thr Leu Thr Leu Arg
 65                  70                  75                  80

Ser Ser Ser Gln Asn Ser Ser Asp Lys Pro Val Ala His Val Val Ala
             85                  90                  95

Asn His Gln Val Glu Glu Gln Leu Glu Trp Leu Ser Gln Arg Ala Asn
        100                 105                 110

Ala Leu Leu Ala Asn Gly Met Asp Leu Lys Asp Asn Gln Leu Val Val
    115                 120                 125

Pro Ala Asp Gly Leu Tyr Leu Val Tyr Ser Gln Val Leu Phe Lys Gly
130                 135                 140

Gln Gly Cys Pro Asp Tyr Val Leu Leu Thr His Thr Val Ser Arg Phe
145                 150                 155                 160

Ala Ile Ser Tyr Gln Glu Lys Val Asn Leu Leu Ser Ala Val Lys Ser
                165                 170                 175

Pro Cys Pro Lys Asp Thr Pro Glu Gly Ala Glu Leu Lys Pro Trp Tyr
            180                 185                 190

Glu Pro Ile Tyr Leu Gly Gly Val Phe Gln Leu Glu Lys Gly Asp Gln
        195                 200                 205

Leu Ser Ala Glu Val Asn Leu Pro Lys Tyr Leu Asp Phe Ala Glu Ser
210                 215                 220

Gly Gln Val Tyr Phe Gly Val Ile Ala Leu
225                 230
```

<210> SEQ ID NO 7
<211> LENGTH: 699
<212> TYPE: DNA
<213> ORGANISM: Homo sapiens

<400> SEQUENCE: 7

```
atgagcactg aaagcatgat ccgggacgtg gagctggccg aggaggcgct ccccaagaag    60
acagggggc cccagggctc caggcggtgc ttgttcctca gcctcttctc cttcctgatc   120
gtggcaggcg ccaccacgct cttctgcctg ctgcactttg gagtgatcgg ccccagagg   180
gaagagttcc caggggacct ctctctaatc agccctctgg cccaggcagt cagatcatct   240
tctcgaaccc cgagtgacaa gcctgtagcc catgttgtag caaaccctca gctgaggg    300
cagctccagt ggctgaaccg ccgggccaat gcctcctgg ccaatggcgt ggagctgaga   360
gataaccagc tggtggtgcc atcagagggc ctgtacctca tctactccca ggtcctcttc   420
aagggccaag ctgcccctc cacccatgtg ctcctcaccc acaccatcag ccgcatcgcc   480
gtctcctacc agaccaaggt caacctcctc tctgccatca gagcccctg ccagagggag   540
accccagagg gggctgaggc caagccctgg tatgagccca tctatctggg aggggtcttc   600
cagctggaga agggtgaccg actcagcgct gagatcaatc ggcccgacta tctcgacttt   660
gccgagtctg gcaggtcta ctttgggatc attgccctg                          699
```

<210> SEQ ID NO 8
<211> LENGTH: 233
<212> TYPE: PRT
<213> ORGANISM: Homo sapiens

<400> SEQUENCE: 8

```
Met Ser Thr Glu Ser Met Ile Arg Asp Val Glu Leu Ala Glu Glu Ala
 1               5                  10                  15

Leu Pro Lys Lys Thr Gly Gly Pro Gln Gly Ser Arg Arg Cys Leu Phe
            20                  25                  30
```

Leu Ser Leu Phe Ser Phe Leu Ile Val Ala Gly Ala Thr Thr Leu Phe
        35                  40                  45
Cys Leu Leu His Phe Gly Val Ile Gly Pro Gln Arg Glu Glu Phe Pro
     50                  55                  60
Arg Asp Leu Ser Leu Ile Ser Pro Leu Ala Gln Ala Val Arg Ser Ser
 65                  70                  75                  80
Ser Arg Thr Pro Ser Asp Lys Pro Val Ala His Val Val Ala Asn Pro
                 85                  90                  95
Gln Ala Glu Gly Gln Leu Gln Trp Leu Asn Arg Arg Ala Asn Ala Leu
            100                 105                 110
Leu Ala Asn Gly Val Glu Leu Arg Asp Asn Gln Leu Val Val Pro Ser
        115                 120                 125
Glu Gly Leu Tyr Leu Ile Tyr Ser Gln Val Leu Phe Lys Gly Gln Gly
    130                 135                 140
Cys Pro Ser Thr His Val Leu Leu Thr His Thr Ile Ser Arg Ile Ala
145                 150                 155                 160
Val Ser Tyr Gln Thr Lys Val Asn Leu Leu Ser Ala Ile Lys Ser Pro
                165                 170                 175
Cys Gln Arg Glu Thr Pro Glu Gly Ala Glu Ala Lys Pro Trp Tyr Glu
            180                 185                 190
Pro Ile Tyr Leu Gly Gly Val Phe Gln Leu Glu Lys Gly Asp Arg Leu
        195                 200                 205
Ser Ala Glu Ile Asn Arg Pro Asp Tyr Leu Asp Phe Ala Glu Ser Gly
    210                 215                 220
Gln Val Tyr Phe Gly Ile Ile Ala Leu
225                 230

<210> SEQ ID NO 9
<211> LENGTH: 2824
<212> TYPE: DNA
<213> ORGANISM: Homo sapiens

<400> SEQUENCE: 9
gctgccacct ctctagaggc acctggcggg gagcctctca acataagaca gtgaccagtc    60
tggtgactca cagccggcac agccatgaac tacccgctaa cgctggaaat ggacctcgag   120
aacctggagg acctgttctg gaactggaca gattggaca actataacga cacctccctg   180
gtggaaaatc atctctgccc tgccacagag gggcccctca tggcctcctt caaggccgtg   240
ttcgtgcccg tggcctacag cctcatcttc ctcctgggcg tgatcggcaa cgtcctggtg   300
ctggtgatcc tggagcggca ccggcagaca cgcagttcca cggagacctt cctgttccac   360
ctggccgtgg ccgacctcct gctggtcttc atcttgccct tgccgtggc cgagggctct   420
gtgggctggg tcctggggac cttcctctgc aaaactgtga ttgccctgca caaagtcaac   480
ttctactgca gcagcctgct cctggcctgc atcgccgtgg accgctacct ggccattgtc   540
cacgccgtcc atgcctaccg ccaccgccgc tcctctccca ccacatcac ctgtgggacc   600
atctggctgg tgggcttcct ccttgccttg ccagagattc tcttcgccaa agtcagccaa   660
ggccatcaca caactccct gccacgttgc accttctccc aagagaacca agcagaaacg   720
catgcctggt tcacctcccg attcctctac catgtggcgg gattcctgct gccatgctg   780
gtgatgggct ggtgctacgt gggggtagtg cacaggttgc gccaggccca gcggcgccct   840
cagcggcaga aggcagtcag ggtggccatc ctggtgacaa gcatcttctt cctctgctgg   900
tcacctacc acatcgtcat cttcctggac accctggcga ggctgaaggc cgtggacaat   960
acctgcaagc tgaatggctc tctccccgtg gccatcacca tgtgtgagtt cctgggcctg  1020

```
gcccactgct gcctcaaccc catgctctac actttcgccg gcgtgaagtt ccgcagtgac    1080
ctgtcgcggc tcctgacgaa gctgggctgt accggccctg cctccctgtg ccagctcttc    1140
cctagctggc gcaggagcag tctctctgag tcagagaatg ccacctctct caccacgttc    1200
taggtcccag tgtccccttt tattgctgct tttccttggg gcaggcagtg atgctggatg    1260
ctccttccaa caggagctgg gatcctaagg gctaccgtg gctaagagtg tcctaggagt     1320
atcctcattt ggggtagcta gaggaaccaa cccccatttc tagaacatcc ctgccagctc    1380
ttctgccggc cctggggcta ggctggagcc caggggagcgg aaagcagctc aaaggcacag   1440
tgaaggctgt ccttacccat ctgcaccccc ctgggctgag agaacctcac gcacctccca    1500
tcctaatcat ccaatgctca agaaacaact tctacttctg cccttgccaa cggagagcgc    1560
ctgcccctcc cagaacacac tccatcagct taggggctgc tgacctccac agcttccct    1620 ctctcctcct gcccacctgt caaacaaagc cagaagctga gcaccagggg atgagtggag    1680
gttaaggctg aggaaaggcc agctggcagc agagtgtggc cttcggacaa ctcagtccct    1740
aaaaacacag acattctgcc aggcccccaa gcctgcagtc atcttgacca agcaggaagc    1800
tcagactggt tgagttcagg tagctgcccc tggctctgac cgaaacagcg ctgggtccac    1860
cccatgtcac cggatcctgg gtggtctgca ggcagggctg actctaggtg cccttggagg    1920
ccagccagtg acctgaggaa gcgtgaaggc cgagaagcaa gaaagaaacc cgacagaggg    1980
aagaaaagag ctttcttccc gaaccccaag gagggagatg gatcaatcaa acccggcggt    2040 ccctccgcc aggcgagatg gggtggggtg gagaactcct agggtggctg ggtccagggg     2100
atgggaggtt gtgggcattg atggggaagg aggctggctt gtccctcct cactcccttc     2160 ccataagcta tagaccccgag gaaactcaga gtcggaacgg agaaaggtgg actgaaggg    2220 gcccgtggga gtcatctcaa ccatcccctc cgtggcatca ccttaggcag ggaagtgtaa    2280
gaaacacact gaggcaggga agtccccagg ccccaggaag ccgtgccctg cccccgtgag    2340
gatgtcactc agatggaacc gcaggaagct gctccgtgct tgtttgctca cctggggtgt    2400
gggaggcccg tccggcagtt ctgggtgctc cctaccacct cccagccctt tgatcaggtg    2460
gggagtcagg gaccctgcc cttgtcccac tcaagccaag cagccaagct ccttgggagg     2520
ccccactggg gaataacag ctgtggctca cgtgagagtg tcttcacggc aggcaacga     2580 ggaagcccta agacgtccct ttttctctg agtatctcct cgcaagctgg gtaatcgatg     2640
ggggagtctg aagcagatgc aaagaggcaa gaggctggat tttgaatttt cttttttaata   2700 aaaaggcacc tataaaacag gtcaatacag tacaggcagc acagagaccc ccggaacaag    2760
cctaaaaatt gtttcaaaat aaaaaccaag aagatgtctt caaaaaaaaa aaaaaaaaa     2820 aaaa                                                                 2824
```

<210> SEQ ID NO 10
<211> LENGTH: 372
<212> TYPE: PRT
<213> ORGANISM: Homo sapiens

<400> SEQUENCE: 10

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

```
Phe Lys Ala Val Phe Val Pro Val Ala Tyr Ser Leu Ile Phe Leu Leu
 50                  55                  60
Gly Val Ile Gly Asn Val Leu Val Leu Val Ile Leu Glu Arg His Arg
 65                  70                  75                  80
Gln Thr Arg Ser Ser Thr Glu Thr Phe Leu Phe His Leu Ala Val Ala
                 85                  90                  95
Asp Leu Leu Val Phe Ile Leu Pro Phe Ala Val Ala Glu Gly Ser
                100                 105                 110
Val Gly Trp Val Leu Gly Thr Phe Leu Cys Lys Thr Val Ile Ala Leu
            115                 120                 125
His Lys Val Asn Phe Tyr Cys Ser Ser Leu Leu Leu Ala Cys Ile Ala
130                 135                 140
Val Asp Arg Tyr Leu Ala Ile Val His Ala Val His Ala Tyr Arg His
145                 150                 155                 160
Arg Arg Leu Leu Ser Ile His Ile Thr Cys Gly Thr Ile Trp Leu Val
                165                 170                 175
Gly Phe Leu Leu Ala Leu Pro Glu Ile Leu Phe Ala Lys Val Ser Gln
            180                 185                 190
Gly His His Asn Asn Ser Leu Pro Arg Cys Thr Phe Ser Gln Glu Asn
            195                 200                 205
Gln Ala Glu Thr His Ala Trp Phe Thr Ser Arg Phe Leu Tyr His Val
210                 215                 220
Ala Gly Phe Leu Leu Pro Met Leu Val Met Gly Trp Cys Tyr Val Gly
225                 230                 235                 240
Val Val His Arg Leu Arg Gln Ala Gln Arg Arg Pro Gln Arg Gln Lys
                245                 250                 255
Ala Val Arg Val Ala Ile Leu Val Thr Ser Ile Phe Phe Leu Cys Trp
            260                 265                 270
Ser Pro Tyr His Ile Val Ile Phe Leu Asp Thr Leu Ala Arg Leu Lys
            275                 280                 285
Ala Val Asp Asn Thr Cys Lys Leu Asn Gly Ser Leu Pro Val Ala Ile
290                 295                 300
Thr Met Cys Glu Phe Leu Gly Leu Ala His Cys Cys Leu Asn Pro Met
305                 310                 315                 320
Leu Tyr Thr Phe Ala Gly Val Lys Phe Arg Ser Asp Leu Ser Arg Leu
                325                 330                 335
Leu Thr Lys Leu Gly Cys Thr Gly Pro Ala Ser Leu Cys Gln Leu Phe
            340                 345                 350
Pro Ser Trp Arg Arg Ser Ser Leu Ser Glu Ser Glu Asn Ala Thr Ser
            355                 360                 365
Leu Thr Thr Phe
    370

<210> SEQ ID NO 11
<211> LENGTH: 2636
<212> TYPE: DNA
<213> ORGANISM: Mus musculus

<400> SEQUENCE: 11
cgacatcaga cagtgaccag cctggtgacg cagagctgca gctatgaact acccactaac    60
cctggacatg ggctccatca catacaatat ggatgacctg tacaaggaac tggccttcta   120
cagtaacagc acggagattc ccctacagga cagtaacttc tgctctacag tcgagggacc   180
cttactgacg tcctttaagg cggtattcat gcctgtggcc tacagcctca tcttcctcct   240
gggtatgatg ggaaacatcc tggtgctggt aatcctggag aggcaccggc acactcggag   300
```

```
ctcaaccgag accttcctgt tccacctcgc agtagccgac cttctcttag tcttcatcct    360
gccttttgca gtggctgagg gctctgtggg ttgggtccta gggaccttcc tctgcaaaac    420
tgtgatcgct ctgcacaaga tcaatttcta ctgcagcagc ctgctgctgg cctgtatagc    480
tgtagaccgg tacctagcca tcgtccatgc tgttcacgcc taccgccgcc gtcgactcct    540
ctccatccac atcacctgca cggccatttg gctggccggc ttcctgttcg ccttaccgga    600
actcctcttt gccaaggttg gccaacctca taacaacgac tccttaccac agtgcacctt    660
ctcccaggaa aacgaagcgg aaactagagc ctggttcacc tcccgtttcc tctaccacat    720
cgggggcttc ctactaccga tgcttgtgat gggatggtgt tacgtgggcg tggtccacag    780
gctactgcag gcccagcggc gccctcagcg cagaaggcg gtcagggtgg ccattttagt     840
gacaagcatt ttcttcctct gctggtcgcc ctaccacatt gtcatcttcc tagatacact    900
ggagaggctg aaggctgtga atagcagctg cgagctgagt ggctatctct ctgtggccat    960
caccttgtgt gaattcctgg gcctggcaca ctgctgtctc aatcccatgc tctacacctt   1020
cgctggcgta aagttccgca gtgacctctc tcggcttctg accaagctgg gctgtgctgg   1080
cccggcctcc ctttgccaac ttttccccaa ctggcgcaag agtagtctct ctgagtcaga   1140
gaatgctact tccctcacca ccttctagat cccggaagtc tcggggcccc tgtctgtttc   1200
tgttttcctt gggaggataa agtggtggcg gaacccatcc aactcgagct ggggccagtg   1260
tccccagatg ggaaagctag ataaactctc tcaaactttc ccaaggggga agcagccca    1320
aaggcaaagc aagctatatc caggccacct gtatcacctt agatgaagag aactccatac   1380
acctcccatc ctaaccagct aaagctaagc tcagctttat ttcttcctgg ccatagggac   1440
aaccacctct gctgtggccc acagtctcat cttcctcctg attatgagcc cagactctcc   1500
tcccagaatg tattccatca tcttaaagac tactggctgc acagctacc caccactcct    1560
ataccacaga ggaatagcca gctggcggcg gcagactatg gccttaatgt gcctgtctca   1620
taaatacaga cttcatgcca gaccttcaac cgtgcctttc tcttaaccaa gcagaaagct   1680
gaaaccgatc tactttaggt agctgtctgg ttccaaccta accagcattg ggtcagcccc   1740
atgttactgg atcttggatt acagactgag ggcaagttcc agaaggttct ggaagctagc   1800
cagtatccta agaagagtaa agggcaagcc agcaggaaag aggcccagtg gaaaagtgga   1860
aagacacctt ttccaggctc taaggaagaa caagtaaaaa tcaaacccag ctgtcttctc   1920
cacccaatgt accaaagctt acagactggt ggggaaatga gatccagggc cctcgtggat   1980
tctacgcacc aatggggaag gaagccaact tgcctgggga agcaagata gcaaagtggt    2040
cctagcctcg agagagggga cacctagcta agagaatgac gacagaggtt cctgtcttca   2100
ttaggcagag gcaatataag aagccaacct gggcaggcaa gtcctcaaac cccaggaagg   2160
cagtaccctg cccctgggag ggtaccactc acatggaacc agaggaagct gctccatgca   2220
tacatagggg aagttagcag gcaattctga gctcggcttc ctcccagcca ccgatctggg   2280
ggcgtggggg taggaagcag agttgcctag taccactcaa gccaaccgta caagctccct   2340
gggggatccc actggggaaa ccaatgctat agcttcagag actgtatcct cattgcagaa   2400
ccgtgaagac acctgggac ccccttttct gctcccagca tccaacaacc agctgggaag    2460
aggcaaaccg ggcacagaaa taaaatgca agagatggca ttttttgaatt ttctcttttt    2520
aataaaaagg cacctataaa acaggtcaat acaggcagag accccggaa caagcctaaa    2580
aagtgtttca aataaaaac aggaagatgt cttcaaaaaa aaaaaaaaaa aaaaaa         2636
```

-continued

<210> SEQ ID NO 12
<211> LENGTH: 374
<212> TYPE: PRT
<213> ORGANISM: Mus musculus

<400> SEQUENCE: 12

Met Asn Tyr Pro Leu Thr Leu Asp Met Gly Ser Ile Thr Tyr Asn Met
1               5                   10                  15

Asp Asp Leu Tyr Lys Glu Leu Ala Phe Tyr Ser Asn Ser Thr Glu Ile
            20                  25                  30

Pro Leu Gln Asp Ser Asn Phe Cys Ser Thr Val Glu Gly Pro Leu Leu
        35                  40                  45

Thr Ser Phe Lys Ala Val Phe Met Pro Val Ala Tyr Ser Leu Ile Phe
    50                  55                  60

Leu Leu Gly Met Met Gly Asn Ile Leu Val Leu Val Ile Leu Glu Arg
65                  70                  75                  80

His Arg His Thr Arg Ser Ser Thr Glu Thr Phe Leu Phe His Leu Ala
                85                  90                  95

Val Ala Asp Leu Leu Leu Val Phe Ile Leu Pro Phe Ala Val Ala Glu
            100                 105                 110

Gly Ser Val Gly Trp Val Leu Gly Thr Phe Leu Cys Lys Thr Val Ile
        115                 120                 125

Ala Leu His Lys Ile Asn Phe Tyr Cys Ser Ser Leu Leu Leu Ala Cys
    130                 135                 140

Ile Ala Val Asp Arg Tyr Leu Ala Ile Val His Ala Val His Ala Tyr
145                 150                 155                 160

Arg Arg Arg Arg Leu Leu Ser Ile His Ile Thr Cys Thr Ala Ile Trp
                165                 170                 175

Leu Ala Gly Phe Leu Phe Ala Leu Pro Glu Leu Leu Phe Ala Lys Val
            180                 185                 190

Gly Gln Pro His Asn Asn Asp Ser Leu Pro Gln Cys Thr Phe Ser Gln
        195                 200                 205

Glu Asn Glu Ala Glu Thr Arg Ala Trp Phe Thr Ser Arg Phe Leu Tyr
    210                 215                 220

His Ile Gly Gly Phe Leu Leu Pro Met Leu Val Met Gly Trp Cys Tyr
225                 230                 235                 240

Val Gly Val Val His Arg Leu Leu Gln Ala Gln Arg Arg Pro Gln Arg
                245                 250                 255

Gln Lys Ala Val Arg Val Ala Ile Leu Val Thr Ser Ile Phe Phe Leu
            260                 265                 270

Cys Trp Ser Pro Tyr His Ile Val Ile Phe Leu Asp Thr Leu Glu Arg
        275                 280                 285

Leu Lys Ala Val Asn Ser Ser Cys Glu Leu Ser Gly Tyr Leu Ser Val
    290                 295                 300

Ala Ile Thr Leu Cys Glu Phe Leu Gly Leu Ala His Cys Cys Leu Asn
305                 310                 315                 320

Pro Met Leu Tyr Thr Phe Ala Gly Val Lys Phe Arg Ser Asp Leu Ser
                325                 330                 335

Arg Leu Leu Thr Lys Leu Gly Cys Ala Gly Pro Ala Ser Leu Cys Gln
            340                 345                 350

Leu Phe Pro Asn Trp Arg Lys Ser Ser Leu Ser Glu Ser Glu Asn Ala
        355                 360                 365

Thr Ser Leu Thr Thr Phe
    370